United States Patent [19]

Buschauer et al.

[11] Patent Number: 4,912,119
[45] Date of Patent: Mar. 27, 1990

[54] IMIDAZOLYLGUANIDINE DERIVATIVES AND COMPOSITIONS CONTAINING THESE COMPOUNDS

[75] Inventors: Armin Buschauer, Berlin; Helmut Schickaneder, Eckental; Peter Morsdorf, Langenzehn; Walter Schunack, Berlin; Gert Baumann, Munich; Kurt-Henning Ahrens, Nuremberg, all of Fed. Rep. of Germany

[73] Assignee: Heumann Pharma GmBH & Co., Nuremberg, Fed. Rep. of Germany

[21] Appl. No.: 95,892

[22] Filed: Sep. 14, 1987

[30] Foreign Application Priority Data

Sep. 15, 1986 [DE] Fed. Rep. of Germany ....... 3631334

[51] Int. Cl.$^4$ ............... A61K 31/415; C07D 233/54
[52] U.S. Cl. .................... 514/333; 514/341; 514/400; 514/397; 546/256; 546/278; 548/342; 548/336
[58] Field of Search ............... 548/342, 336; 546/256, 546/278; 514/333, 341, 400, 397

[56] References Cited

U.S. PATENT DOCUMENTS 4,098,898  7/1978  Durant et al. .................. 548/342
4,379,158  4/1983  Hirata et al. .................. 548/342

FOREIGN PATENT DOCUMENTS 3528214  2/1987  Fed. Rep. of Germany ...... 548/342

*Primary Examiner*—Mary C. Lee
*Assistant Examiner*—Zinna Northington
*Attorney, Agent, or Firm*—Burns, Doane, Swecker & Mathis

[57] ABSTRACT

New imidazolyl guanidine derivatives corresponding to the following general formula

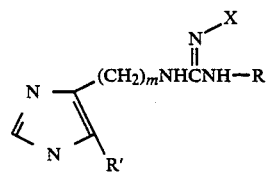

are described. These compounds may be used in cardiac diseases, certain forms of hypertension and in diseases of arterial occlusion on account of their agonistic action on histamine-$H_2$ receptors and in part their additional $H_1$-antagonistic receptor activity.

18 Claims, No Drawings

IMIDAZOLYLGUANIDINE DERIVATIVES AND COMPOSITIONS CONTAINING THESE COMPOUNDS

BACKGROUND OF THE INVENTION

The present invention relates to new imidazolyl guanidine derivatives which by virtue of their agonistic action on histamine-$H_2$ receptors and in part also their additional $H_1$-antagonistic receptor activity may be used in cardiac diseases, certain forms of hypertension and diseases of arterial occlusion. Histamine used as specific stimulator of the $H_2$ receptors produces adverse, in some cases lethal effects in the form of bronchospasm and anaphylactic shock due to its $H_1$-agonistic action and therefore cannot be used therapeutically for the treatment of the above-mentioned disorders.

It is therefore an object of the present invention to compensate for the disadvantageous effects of histamine and provide better and more selectively acting $H_2$-agonists in which the harmful side effects due to an $H_1$-agonistic active component may be avoided by an additional $H_1$-antagonistic activity profile.

This problem is solved by the present invention.

SUMMARY OF THE INVENTION

The invention relates to imidazolyl guanidine derivatives corresponding to the general formula I

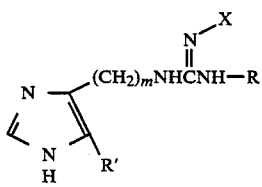

wherein R denotes the group

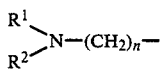

in which $R^1$ stands for an unsubstituted or a mono- to tri-substituted phenyl group or an unsubstituted or a mono- to tri-substituted pyridine ring, $R^2$ stands for a hydrogen atom, a $C_1$-$C_3$-alkyl group, an optionally mono- to tri-substituted phenyl group, an unsubstituted or a mono- to tri-substituted benzyl group or an unsubstituted or a mono- to tri-substituted heteroarylmethyl group and n has the value 2, 3 or 4, or wherein R denotes the group

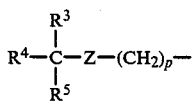

wherein $R^3$ stands for an unsubstituted or a mono- to tri-substituted phenyl group or an unsubstituted or a mono- to tri-substituted pyridine ring, $R^4$ stands for a hydrogen atom or an optionally mono- to tri-substituted phenyl group, $R^5$ stands for a hydrogen atom or a methyl or hydroxyl group and Z stands for a single bond or an oxygen atom and p has the value 2 or 3, X denotes a hydrogen atom or a benzoyl group, m has the value 2 or 3 and R' denotes a hydrogen atom or a methyl group, and the physiologically acceptable salts thereof.

DESCRIPTION OF THE PREFERRED EMBODIMENT

In the general formula I, the symbol R may denote the group

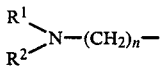

In this group, $R^1$ may stand for an unsubstituted or a mono- to tri-substituted phenyl group, preferably a disubstituted phenyl group. Substituents, if present, may consist in particular of 1 to 3 halogen atoms such as fluorine, chlorine or bromine atoms, preferably fluorine or chlorine atoms, 1 to 3 $C_1$-$C_3$-alkyl groups, preferably methyl or ethyl groups, and 1 to 3 $C_1$-$C_3$-alkoxy groups such as methoxy or ethoxy groups. Monosubstitution and disubstitution are preferred. Monosubstitution is preferably in the 4-position and disubstitution is preferably in the 3- and 4-positions of the phenyl ring. The trifluoromethyl group may also be used as substituent on the phenyl ring. The phenyl group is preferably substituted with 1 to 3 trifluoromethyl groups, most preferably one trifluoromethyl group. In that case, the substituent is preferably attached in the 4-position of the phenyl ring.

The substituent $R^1$ may also be an unsubstituted or a mono- to tri-substituted pyridine ring. In the case of multiple substitution, the pyridine ring is preferably mono- or di-substituted. Suitable substituents for the pyridine ring include, for example, halogen atoms such as fluorine, chlorine or bromine atoms, fluorine and chlorine atoms being preferred, especially fluorine atoms; $C_1$-$C_3$-alkyl groups such as methyl or ethyl groups; and $C_1$-$C_3$-alkoxy groups such as methoxy, ethoxy or propoxy groups, methoxy groups being preferred.

The attachment of the pyridine ring denoted by $R^1$ to the nitrogen atom in the group R may take place in the 2-, 3- or 4-position of the pyridine ring, the 2- or 3-position being preferred. Linkage in the 2-position of the pyridine ring is particularly preferred.

$R^2$ stands for a hydrogen atom, a $C_1$-$C_3$-alkyl group, in particular a methyl, ethyl or propyl group, a phenyl group which may be unsubstituted or optionally mono- to tri-substituted, in particular mono- or di-substituted, a benzyl group which may be unsubstituted or mono- to tri-substituted, or a heteroarylmethyl group which may be unsubstituted or mono- to tri-substituted. In the case of substitution, the phenyl group denoted by $R^2$ may be substituted in the same manner and with the same substituents as described above with reference to the substitution on the phenyl group denoted by $R^1$.

In the case of substitution, the benzyl group may be substituted with 1 to 3, preferably 2 halogen atoms such as fluorine, chlorine or bromine atoms, preferably chlorine or fluorine atoms, or $C_1$-$C_3$-alkoxy groups such as methoxy or ethoxy groups, preferably methoxy groups. In the case of monosubstitution of the benzyl group denoted by $R^2$, the substituent is preferably attached in the para position to the methylene group whereas in the case of di-substitution the 3- and 4-positions of the benzyl group are preferred. The benzyl group denoted by $R^2$ may also be substituted with trifluoromethyl, in particular with 1 to 3 trifluoromethyl groups. Monosubstitution with the trifluoromethyl group is preferred, and the trifluoromethyl group is preferably attached to the benzyl group in the para-position.

When $R^2$ stands for a heteroarylmethyl group, this group is preferably a thiophenylmethyl, furanmethyl or pyridine methyl group. The heteroarylmethyl group may also be unsubstituted but is preferably mono- to tri-substituted. Mono- or di-substitution are preferred. Suitable substituents include halogen atoms such as fluorine, chlorine or bromine atoms, $C_1$–$C_3$-alkyl groups such as methyl or ethyl groups and straight chained $C_1$–$C_3$-alkoxy groups such as methoxy groups.

n has the value 2, 3 or 4, the value 3 being preferred.

R may also denote the group $$R^4-\underset{\underset{R^5}{|}}{\overset{\overset{R^3}{|}}{C}}-Z-(CH_2)_p-.$$

In this group, $R^3$ may stand for an unsubstituted or a mono- to tri-substituted phenyl group or a mono- to tri-substituted pyridine ring. Substituents, if present, may be, in particular, 1 to 3 halogen atoms such as fluorine, chlorine or bromine atoms, preferably fluorine or chlorine atoms, one to three $C_1$–$C_3$-alkyl groups, preferably methyl or ethyl groups, and 1 to 3 $C_1$–$C_3$-alkoxy groups such as methoxy or ethoxy groups. Monosubstitution and disubstitution are preferred. Monosubstitution preferably takes place in the 4-position and di-substitution preferably in the 3 and 4-positions of the phenyl ring. The trifluoromethyl group and the hydroxyl group may also be used as substituents for the phenyl ring. The phenyl group is preferably substituted with a trifluoromethyl group or a hydroxyl group, the substituent being preferably attached in the 4-position of the phenyl ring. The substituent $R^3$ may also be an unsubstituted or a mono- to tri-substituted pyridine ring, preferably an unsubstituted pyridine ring or a monosubstituted pyridine ring. Suitable substituents for the pyridine ring include, for example, halogen atoms such as fluorine, chlorine or bromine atoms, fluorine or chlorine atoms being preferred, especially fluorine atoms; $C_1$–$C_3$-alkyl groups such as methyl or ethyl groups and $C_1$–$C_3$-alkoxy groups such as methoxy, ethoxy or propoxy groups, methoxy groups being preferred.

The pyridine ring denoted by $R^3$ may be attached to the nitrogen atom in group R in the 2-, 3- or 4-position of the pyridine ring, the 2- or 3-position being preferred. Attachment in the 2-position of the pyridine ring is particularly preferred.

$R^4$ stands for a hydrogen atoms or an unsubstituted or a mono- to tri-substituted phenyl group. In the case of substitution, the phenyl group denoted by $R^4$ is substituted in the same manner as the phenyl group denoted by $R^3$, $R^5$ denotes a hydrogen atom or a methyl or hydroxyl group. Z stands for a single bond or an oxygen atom, and p has the value 2 or 3.

In the general formula I, X denotes a hydrogen atom or a benzoyl group, m has the value 2 or 3, preferably 3, and R' denotes a hydrogen atom or a methyl group, preferably a hydrogen atom.

In a preferred group of compounds according to the invention, R in the general formula I denotes the group

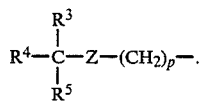

wherein $R^1$ stands for an unsubstituted or a mono- to tri-substituted, preferably a mono- or di-substituted, most preferably an unsubstituted pyridine ring. If the pyridine ring is substituted, the substituents may be halogen atoms, for example a fluorine, chlorine or bromine atom, preferably a fluorine or chlorine atom, in particular a fluorine atom, $C_1$–$C_3$-alkyl groups such as a methyl or ethyl group, or $C_1$–$C_3$-alkoxy groups such as a methoxy, ethoxy or propoxy group, preferably a methoxy group.

The attachment of the pyridine ring to the nitrogen atom in R may be in the 2-, 3- or 4-position of the pyridine ring, the 2- or 3-position being preferred, the 2-position of the pyridine ring being particularly preferred.

$R^2$ stands for an optionally mono- to tri-substituted benzyl group or an unsubstituted or mono- to tri-substituted heteroarylmethyl group. The benzyl group may be substituted, for example, with 1 to 3, preferably 2 halogen atoms such as a fluorine, chlorine or bromine atom, preferably a chlorine or fluorine atom, or a $C_1$–$C_3$-alkoxy group such as a methoxy or ethoxy group, preferably a methoxy group, and the substituent is preferably attached in the para-position to the methylene group. In the case of disubstitution, the 3- and 4-positions of the benzyl group are preferred.

The $CF_3$ group may be used as further substituent, the trifluoromethyl group is preferably attached in the para-position of the benzyl group.

The heteroarylmethyl group may be, for example, a thiophenemethyl group, a furanmethyl group or a pyridine methyl group, optionally substituted with one or two halogen atoms such as fluorine, chlorine or bromine atoms, a $C_1$–$C_3$-alkyl group, for example a methyl or ethyl group, or a straight chained $C_1$–$C_3$-alkoxy group, for example a methoxy group.

In this preferred group of compounds according to the present invention, n has the value 2, 3 or 4, preferably 2 or 3; X and R' preferably denote a hydrogen atom and m has the value 2 or 3, preferably 3.

In another preferred group of compounds according to the invention, R denotes the group

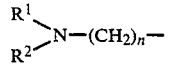

wherein $R^1$ stands for an unsubstituted or a mono- to tri-substituted phenyl ring. The phenyl ring may be substituted with 1 to 3 halogen atoms such as fluorine, chlorine or bromine atoms, preferably fluorine or chlorine atoms, $C_1$–$C_3$-alkyl groups, preferably methyl or ethyl groups, or $C_1$–$C_3$-alkoxy groups such as methoxy or ethoxy groups which are preferably situated in the 4-position or, in the case of di-substitution, in the 3- and 4-positions. Another preferred substituent is the trifluoromethyl group, which is preferably attached in the 4-position of the phenyl ring.

$R^2$ denotes an unsubstituted or a mono- to tri-substituted heteroarylmethyl group; for example, a thiophene methyl group, a furanmethyl group or a pyridinemethyl group, preferably a thiophene methyl group.

The same applies to the substitution of this heteroarylmethyl group as to the one already described above.

The index n has the value 2, 3 or 4, preferably 2 or 3, the value 2 being particularly preferred. X and R' preferably stand for a hydrogen atom and m has the value 2 or 3, preferably 3.

In another preferred group of compounds according to the invention of the general formula I, R denotes the group

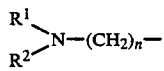

wherein $R^1$ stands for an unsubstituted or a mono- to tri-substituted, preferably an unsubstituted, pyridine ring and $R^2$ stands for a hydrogen atom. If the pyridine ring is multisubstituted, 1 to 3 identical or different substituents selected from halogen atoms, straight chained $C_1$-$C_3$-alkyl groups and straight chained $C_1$-$C_3$-alkoxy groups are considered. The pyridine ring may be attached to the nitrogen atom in the 2-, 3- or 4-position, the 2- and 3-positions being preferred, especially the 2-position.

n has the value 2, 3 or 4, preferably 3. X and R' preferably stand for a hydrogen atom and m has the value 2 or 3, preferably 3.

In another preferred group of compounds according to the invention, R in the general formula I denotes the group

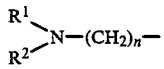

wherein $R^1$ stands for an unsubstituted or a mono- to tri-substituted pyridine ring and $R^2$ stands for an unsubstituted or a mono- to tri-substituted phenyl ring. If the pyridine ring or the phenyl ring is substituted, the substituents are preferably halogen atoms, for example fluorine, chlorine or bromine atoms, preferably fluorine or chlorine atoms, or straight chained $C_1$-$C_3$-alkoxy groups such as methoxy or ethoxy groups, preferably a methoxy group, or straight chained $C_1$-$C_3$-alkyl groups, for example a methyl or ehtyl group, preferably a methyl group.

The pyridine ring may be attached to the nitrogen atom in R in the 2-, 3- or 4-position, the 2-position being particularly preferred. In that case, any substituents present are in the 3- and/or 5-positions.

If the phenyl ring is monosubstituted, then substitution in the 4-position is preferred. Substitution with a chlorine or fluorine atom in the 4-position is particularly preferred. If the phenyl ring is disubstituted, then substitution in the 3- and 4-positions are preferred. The trifluoromethyl group is also a preferred substituent and is preferably attached in the 4-position of the phenyl ring. X and R' preferably stand for a hydrogen atom, n has the value 2, 3 or 4, preferably the value 3, and m preferably has the value 3.

In another preferred group of compounds according to the invention, R in the general formula I denotes the group

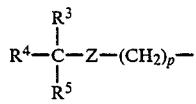

wherein $R^3$ and $R^4$, which may be identical or different, represent each an unsubstituted or a mono- to tri-substituted phenyl group. The substituents may be, for example, halogen atoms such as fluorine, chlorine or bromine atoms, straight chained $C_1$-$C_3$-alkoxy groups such as, preferably, methoxy groups, or straight chained $C_1$-$C_3$-alkyl groups, preferably methyl or ethyl groups. Halogen atoms, in particular fluorine or chlorine atoms, are preferred as substituents in the 2-, 3- or, preferably the 4-position or, in the case of disubstitution, in the 3-/4- or 3-/5-positions, preferably in the 3-/4-position of the phenyl ring. The trifluoromethyl group is also a preferred substituent and is preferably situated in the 4-position of the phenyl ring.

$R^5$ stands for a hydrogen atom or a methyl group, as already defined above, Z stands for a single bond and p has the value 2 or 3, preferably the value 2. X and R' preferably stand for a hydrogen atom and m preferably has the value 3.

In another preferred group of compounds according to the invention corresponding to the general formula I, R denotes the group

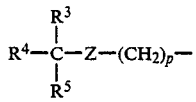

wherein $R^4$ stands for an unsubstituted or a mono- to tri-substituted phenyl group. If the phenyl group is substituted, the substituents are preferably halogen atoms such as fluorine, chlorine or bromine atoms, in particular fluorine or chlorine atoms, straight chained $C_1$-$C_3$-alkoxy groups, for example a methoxy, ethoxy, or propoxy group, and straight chained $C_1$-$C_3$-alkyl groups, such as methyl or ethyl groups or a hydroxyl group. The substituents are then preferably in the 4-position or, in the case of disubstitution, in the 2-/6-, 3-/5- or 3-/4-positions but any other conceivable substitutions are possible. Particularly preferred is that group of compounds according to the invention in which $R^4$ stands for a 4-fluorophenyl, 4-chlorophenyl, 3,4-/3,5-difluorophenyl or 3,4-/3,5-dichlorophenyl group. A disubstituted group denoted by $R^3$ may also be, for example, a 4-fluoro-3-chlorophenyl group or a 4-chloro-3-fluorophenyl group.

The trifluoromethyl group is also a preferred substituent. This may be attached in the 2-, 3- or 4-position of the phenyl ring, preferably in the 3- and 4-position, most preferably in the 4-position.

$R^3$ stands for an unsubstituted or a mono- to tri-substituted pyridine ring which may be attached at the 2-, 3- or 4-position, the 2- and 3-positions being particularly preferred. The substituents on the pyridine ring may be halogen atoms, for example fluorine, chlorine or bromine atoms, preferably bromine atoms, $C_1$-$C_3$-alkyl groups such as methyl or ethyl groups, preferably methyl groups, or $C_1$-$C_3$-alkoxy groups such as methoxy or ethoxy groups, in particularly methoxy groups. If the pyridine ring is attached through the 2-position, which is mentioned above as particularly preferred, then any substituents present are in the 3- and/or 5-position of the pyridine ring. $R^5$ stands for a hydrogen atom or a methyl or hydroxyl group, preferably a hydrogen atom, Z stands for a single bond and p has the value 2 to 3, most preferably the value 2. X represents a hydrogen atom, R' represents a hydrogen atom or a methyl group, preferably a hydrogen atom, and m has the value 2 or 3, in particular the value 3.

In another preferred group of compounds according to the invention, R in the general formula I denotes the group

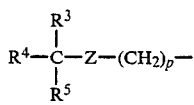

wherein $R^3$ stands for an unsubstituted or a mono- to tri-substituted pyridine ring and $R^4$ and $R^5$ stand each for a hydrogen atom. The pyridine ring is preferably unsubstituted but may be mono- to tri-substituted with halogen atoms such as fluorine, chlorine or bromine atoms, $C_1$-$C_3$-alkyl groups such as methyl, ethyl or propyl groups or $C_1$-$C_3$-alkoxy groups such as methoxy, ethoxy or propoxy groups.

Z stands for a single bond, p has the value 2 or 3, preferably 3, X and R' denote each a hydrogen atom and m preferably has the value 3.

In another preferred group of compounds according to the invention, R in the general formula I denotes the group

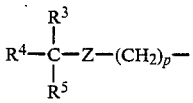

wherein $R^3$ and $R^4$, which may be identical or different, represent, independently of one another, an unsubstituted or a mono- to tri-substituted phenyl ring. The substituents on the phenyl ring, which are preferably in the 3- or 4-position, in particular in the 4-position, may be halogen atoms such as fluorine or chlorine atoms, $C_1$-$C_3$-alkyl groups such as, for example, methyl, ethyl or propyl groups, or $C_1$-$C_3$-alkoxy groups, preferably methoxy groups. In this preferred group of compounds according to the invention, $R^5$ stands for a hydrogen atom, Z stands for an oxygen atom and p may have the value 2 or 3, preferably 2. X and R' preferably stand for a hydrogen atom and m preferably has the value 3.

Compounds according to the invention corresponding to the general formula I in which R, R' and m have the meanings defined above and X denotes a benzoyl group may be prepared by two different variations of the process, namely (a₁) by the reaction of a compound corresponding to the general formula II

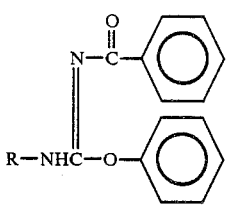

(II)

wherein R has the meaning indicated above with a compound corresponding to the general formula III

(III)

wherein R' and m have the meanings indicated above, to form a compound corresponding to the general formula I.

The components are preferably reacted together in equimolar quantities and in a polar solvent, for example an alcohol such as methanol, ethanol or isopropanol, preferably ethanol, or in acetonitrile, dimethylsulphoxide, dimethylformamide or pyridine, preferably in acetonitrile, at temperatures from room temperature to the reflux temperature of the solvent used.

(a₂) or by the reaction of a compound corresponding to the general formula IV

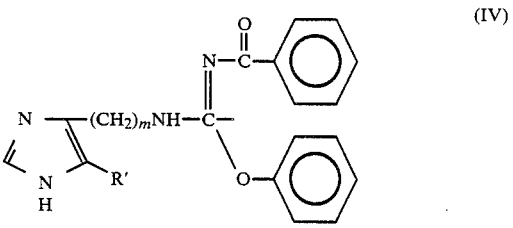

(IV)

wherein R' and m have the meanings indicated above with a compound corresponding to the general formula V

R—NH₂ (V)

wherein R has the meaning defined above, to form a compound corresponding to the general formula I.

The quantities used, the solvents and the reaction conditions are the same as described above with reference to the process variation (a₁).

Compounds according to the invention corresponding to the general formula I in which R, R' and m have the meanings defined above and X denotes a hydrogen atom may be prepared by one of the following four process variations:

(b₁) By hydrolysis of a compound corresponding to the general formula Ia

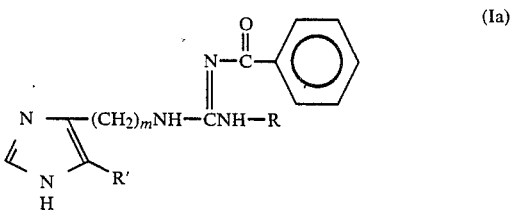

(Ia)

wherein R, R' and m have the meanings defined above.

This hydrolysis may be carried out under acid or alkaline conditions, acid hydrolysis being preferred, for example with dilute sulphuric acid or dilute hydrochloric acid, in particular hydrochloric acid. Hydrolysis is carried out at elevated temperatures, preferably at the reflux temperature.

(b₂) By hydrolysis of a compound corresponding to the general formula VI

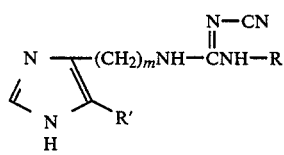

wherein R, R' and m have the meanings indicated above by means of an acid, for example dilute sulphuric acid or dilute hydrochloric acid, preferably hydrochloric acid as indicated above, to form a compound corresponding to formula I.

(b₃) By the reaction of a compound corresponding to the general formula VII

wherein R has the meaning indicated above with a compound corresponding to the general formula III

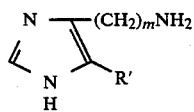

wherein R' and m have the meanings indicated above to form a compound corresponding to the general formula I.

The reaction is carried out in a polar solvent such as pyridine or acetonitrile, preferably in acetonitrile, and at the reflux temperature of the solvent used.

(b₄) By the reaction of a compound corresponding to the general formula VIII

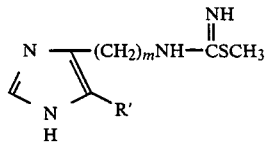

wherein R' and m have the meanings defined above with a compound corresponding to the general formula V

   (V)

wherein R has the meaning indicated above to form a compound corresponding to the general formula I.

This reaction is also carried out in a polar solvent such as pyridine or acetonitrile, preferably acetonitrile, and at the reflux temperature of the solvent used.

The compounds obtained by the individual variations of the process may be isolated and purified by the conventional methods, for example by chromatographic methods, recrystallisation, etc.

The compounds obtained by the individual variations of the process may be converted into physiologically acceptable salts thereof.

The present invention therefore covers not only the stereoisomeric compounds and hydrates of the substances corresponding to the general formula I but also the physiologically acceptable salts of these compounds. These salts may be, for example, salts with mineral acids such as hydrochloric, hydrobromic or hydriodic acid, phosphoric acid, metaphosphoric acid, nitric acid or sulphuric acid or salts with organic acids such as formic acid, acetic acid, propionic acid, phenylacetic acid, tartaric acid, citric acid, fumaric acid, methane sulphonic acid, embonic acid, etc.

The compounds according to the invention may be formulated as desired for administration. The invention therefore also covers medicaments containing at least one compound according to the invention for use in human and veterinary medicine. These medicaments may be prepared by the conventional methods using one or more pharmaceutical carriers or diluents.

The compounds according to the invention may therefore be formulated for oral, buccal, topical, parenteral or rectal administration.

For oral administration, the medicament may be provided, for example, in the form of tablets, capsules, powders, solutions, syrups or suspensions which have been prepared by conventional methods using acceptable diluents.

For buccal administration, the medicament may take the form of tablets or sachets formulated in the usual manner.

The compounds according to the invention may be formulated for parenteral administration by bolus injection or continuous infusion. Formulations for injection may be provided in the form of ampoules containing single doses or they may be provided in multiple dose containers with added preservative.

The medicaments may assume forms such as suspensions, solutions or emulsions in oily or aqueous carriers and they may contain formulating auxiliaries such as suspending or dispersing agents and/or stabilisers.

Alternatively, the active ingredient may be provided in powder form to be reconstituted before use with a suitable carrier, for example with sterile, pyrogen-free water.

The compounds according to the invention may also be formulated as rectal preparations such as suppositories or retention enemas which may contain, for example, conventional suppository excipients such as cocoa butter or other glycerides.

For topical application, the compounds according to the invention may be formulated in the usual manner as ointments, creams, gels, lotions, powders or sprays.

For oral administration, a suitable daily dose of compounds according to the invention is composed of 1 to 4 doses with a total of 5 mg to 1 g per day, depending on the patient's condition. In individual cases, it may be necessary to deviate from the quantities mentioned, depending on the individual response of the patient to the active ingredient and the nature of its formulation and the point in time or time interval at which administration takes place. Thus, for example, in some cases it may be sufficient to administer less than the minimum quantity indicated above whereas in others it may be necessary to exceed the upper limit.

The compounds according to this invention are distinguished by a novel, hitherto unknown and undescribed pharmacological overall activity. The new class of structure according to this invention has both a H₁-antagonistic active component and an H₂-agonistic component. These manifest the pharmacological results shown below. One recognized method of determining the H₁-antagonistic activity is the determination of the pA$_2$-values in vitro (O. Arunlakshana and H. O. Schild, (1959), "Some Quantitative Uses of Drug Antagonists", Br. J. Pharmac. Chemother, 14, 48–58). To determine the H$_2$-agonistic activity (pD$_2$-values), the method of J. M. van Rossum, (1963) is employed, described in "Cumulative Dose-Response Curves II. Technique for the Making of Dose-Response Curves in Isolated Organs and the Evaluation of Drug Parameters", Arch. Intern. Pharmacodyn. Therap. 143, 299–307.

| Pharmacological Data (determined on isolated atrium and ileum of guinea-pig) | | |
|---|---|---|
| | pD$_2$-value (Atrium) | pA$_2$-value (Ileum) |
| Example 2 | 6.95 | 6.51 |
| Example 3 | 5.67 | 8.60 |
| Example 4 | 6.36 | 8.04 |
| Example 8 | 6.91 | 7.43 |
| Example 14 | 8.20 | 6.94 |
| Example 16 | 7.86 | 6.95 |
| Example 17 | 8.12 | 7.07 |
| Example 18 | 8.05 | 6.55 |
| Example 20 | 7.94 | 7.05 |
| Example 24 | 8.09 | 6.71 |

EXAMPLE 1

N$^1$-[3-(1H-imidazol-4-yl)propyl]-N$^2$-[3-(pyridin-2-yl)propyl]-guanidine

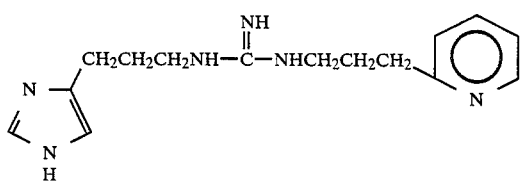

(a) N$^1$-Benzoyl-N$^2$[3-(pyridin-2-yl)propyl]-thiourea

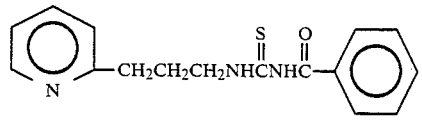

3.30 g (24 mmol) of 3-(pyridin-2-yl)-propylamine and 3.95 g (24 mmol) of benzoylisothiocyanate are boiled under reflux in 100 ml of dichloromethane for 2 hours. After removal of the solvent by evaporation under vacuum, the residue is recrystallized from MTBE. 5.16 g (71%) of colourless crystals melting at 85°–86° C. are obtained.

C$_{15}$H$_{17}$N$_3$OS (299.4).

(b) S-Methyl-N-[3-(pyridin-2-yl)propyl]-isothiuronium iodide

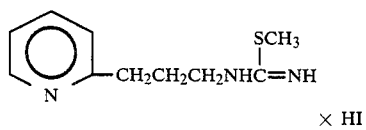

4.50 g (15 mmol) of N$^1$-Benzoyl-N$^2$-[3-(pyridin-2-yl)propyl]-thiourea are boiled in 200 ml of methanol and 60 ml of water together with 4.15 g (30 mmol) of potassium carbonate for 40 minutes. After removal of the solvent by evaporation under vacuum, the residue is taken up with 20 ml of water and the aqueous phase is extracted four times with 30 ml portions of dichloromethane. The combined organic phases are dehydrated with sodium sulphate, filtered and evaporated under vacuum. The residue is taken up in 100 ml of ethanol and stirred together with 1.2 ml (19 mmol) of methyl iodide for 20 hours at room temperature. After removal of the solvent by evaporation under vacuum, the residue is crystallized from MTBE.

3.52 g (69%) of colourless crystals melting at 131°–132° C.

C$_{10}$H$_{16}$IN$_3$S (337.2).

(c) N$^1$-[3-(1H-Imidazol-4-yl)propyl]-N$^2$-[3-(pyridin-2-yl)propyl]-guanidine 1.00 g (3.0 mmol) of S-methyl-N-[3-(pyridin)-2-yl)propyl]-isothiuronium iodide and 0.40 g (3.2 mmol) of 3-(1H-imidazol-4-yl)-propylamine are boiled under reflux in 20 ml of acetonitrile for 3 hours. After removal of the solvent by evaporation under vacuum, the residue obtained is chromatographed on aluminium oxide (neutral) with ethanol/ethyl acetate (1:1). After concentration by evaporation under vacuum, the main fraction yields 0.75 g (88%) of a pale yellow, amorphous solid.

C$_{15}$H$_{22}$N$_6$ (286.4).

| $^1$H-NMR data: (DMSO-d$_6$, TMS as internal standard) | $\delta$ = 1.6–2.2 (m) 4 H, <br> 2.5 (t) 2H, <br> 2.8 (t) 2 H, <br> 3.1–3.5 (m) 4 H, <br> 6.9 (s) 1 H, <br> 7.2–8.0 (m) 8 H, 4 H replaceable by D$_2$O, <br> 8.6 (dd) 1 H ppm. |
|---|---|

EXAMPLE 2

N$^1$-[3-(1H-Imidazol-4-yl)propyl]-N$^2$-[4-(pyridin-2-yl)butyl]-guanidine hydriodide

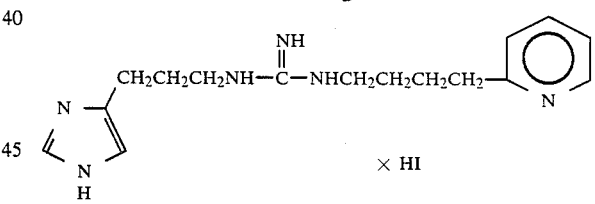

(a) N$^1$-Benzoyl-N$^2$-[4-(pyridin-2-yl)butyl]-thiourea

Prepared by a method analogous to that of Example 1(a) from 17.7 g (118 mmol) of 4-(pyridin-2-yl)-butylamine and 19.2 g (118 mmol) of benzoyl isothiocyanate. Chromatographic purification of the crude product on silica gel with dichloromethane/methanol (95:5) as solvent yields 28.4 g (77%) of a reddish, viscous oil.

C$_{17}$H$_{19}$N$_3$OS (313.4).

(b) S-Methyl-N-[4-(pyridin-2-yl)butyl]-isothiuronium iodide

From N$^1$-benzoyl-N$^2$-[4-(pyridin-2-yl)butyl]-thiourea by a method analogous to that of Example 1(b). Pale yellow needles melting at 105°–106° C. after recrystallization from ethanol/ethyl acetate (1:4).

C$_{11}$H$_{18}$IN$_3$S (351.2).

(c) N$^1$-[3-(1H-Imidazol-4-yl)propyl]-N$^2$-[4-(pyridin-2-yl)butyl]-guanidine hydriodide 2.00 g (5.7 mmol) of S-methyl-N-[4-(pyridin-2-yl)butyl]-isothiuronium iodide and 0.85 g (6.8 mmol) of 3-(1H-imidazol-4-yl)-propylamine are boiled in 20 ml of acetonitrile for 2 hours. After removal of the solvent by evaporation under vacuum, the residue is chromatographed on silica gel with dichloromethane/methanol (8:2). The main fraction yields 1.32 g (54%) of a yellowish, amorphous solid after evaporation.

$C_{16}H_{25}IN_6$ (428.3).

| $^1$H-NMR data: (CD$_3$OD, TMS as internal standard) | δ = 1.5–2.2 (m) 6 H, 2.7–3.0 (m) 4 H, 3.2–3.5 (m) 4 H, 5.0 (broad) 5 H, replaceable by D$_2$O, 7.2 (s) 1 H, 7.2–8.0 (m) 3 H, 8.3 (s) 1 H, 8.5 (dd) 1 H ppm. |
|---|---|

EXAMPLE 3

$N^1$-[3-(1H-Imidazol-4-yl)propyl]-$N^2$-[3-[N-(4-chlorobenzyl)-N-(pyridin-2-yl)amino]propyl]-guanidine hydriodide

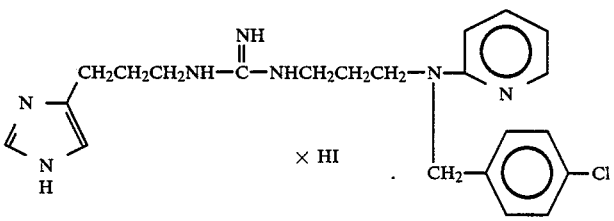

(a) $N^1$-Benzoyl-$N^2$-[3-[N-(4-chlorobenzyl)-N-(pyridin-2-yl)amino]propyl]-thiourea Prepared by a method analogous to that of Example 1(a) from 2.76 g (10 mmol) of N-(4-chlorobenzyl)-N-(pyridin-2-yl)-1,3-propanediamine and 1.63 g (10 mmol) of benzoyl isothiocyanate. 3.63 g (83%) of a pale yellow oil.

$C_{26}H_{23}ClN_4OS$ (438.5).

(b) S-Methyl-N-[3-[N-(4-chlorobenzyl)-N-(pyridin-2-yl)amino]propyl]-isothiuronium iodide Obtained from $N^1$-benzoyl-$N^2$-[3-[N-(4-chlorobenzyl)-N-(pyridin-2-yl)amino]propyl]-thiourea by a method analogous to that of Example 1(b) in the form of a pale yellow, amorphous solid.

$C_{17}H_{22}ClIN_4S$ (680.6).

(c) $N^1$-[3-(1H-Imidazol-4-yl)propyl]-$N^2$-[3-[N-(4-chlorobenzyl)-N-(pyridin-2-yl)amino]propyl]-guanidine hydriodide 1.00 g (2.1 mmol) of S-methyl-N-[3-[N-(4-chlorobenzyl)-N-(pyridin-2-yl)amino]propyl]-isothiuronium iodide and 0.26 g (2.1 mmol) of 3-(1H-imidazol-4-yl)-propylamine are boiled in 15 ml of acetonitrile for 3 hours. The residue obtained after evaporation of the solvent under vacuum is chromatographed on silica gel with ethyl acetate/methanol (7:3) as solvent. 0.17 g (15%) of a colourless, amorphous solid is obtained.

$C_{22}H_{29}ClIN_7$ (553.9).

| $^1$H-NMR data: (CD$_3$OD, TMS as internal standard) | δ = 1.7–2.1 (m) 4 H, 2.7 (t) 2 H, 3.1–3.4 (m) 4 H, 3.6 (t) 2 H, 4.7 (s) 2 H, 4.8 (broad) 5 H, replaceable by D$_2$O, 6.6–7.7 (m) 8 H, |
|---|---|

-continued

| | 7.7 (s) 1 H, 8.2 (dd) 1 H ppm. |
|---|---|

EXAMPLE 4

$N^1$-[3-(1H-Imidazol-4-yl)propyl]-$N^2$[2-[N-(pyridin-2-yl)-N-(thiophen-2-yl-methyl)amino]ethyl]-guanidine hydriodide

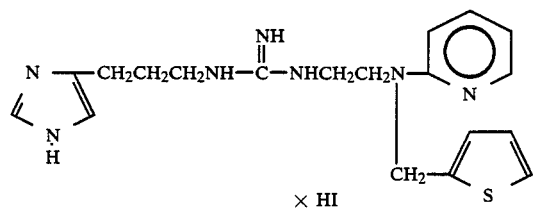

(a) $N^1$-Benzoyl-$N^2$-[2-[N-(pyridin-2-yl)-N-(thiophen-2-yl-methyl)amino]ethyl]-thiourea Prepared by a method analogous to that of Example 1(a) from 2.00 g (8.6 mmol) of N-(pyridin-2-yl)-N-(thiophen-2-yl-methyl)-ethylenediamine and 1.40 g (8.6 mmol) of benzoyl isothiocyanate. The crude product is purified on silica gel with dichloromethane/methanol (99:1) as solvent. 2.85 g (84%) of a pale yellow, viscous oil is obtained from the main fraction after evaporative concentration under vacuum.

$C_{20}H_{20}N_4OS_2$ (396.5).

(b) S-Methyl-N-[2-[N-(pyridin-2-yl)-N-(thiophen-2-yl-methyl)amino]ethyl]-isothiuronium iodide 1.84 g (85%) of a colourless, amorphous solid are obtained by a method analogous to that of Example 1(b) from 2.00 g (5 mmol) of $N^1$-benzoyl-$N^2$-[2[N-(pyridin-2-yl)-N-(thiophen-2-yl-methyl)amino]ethyl]-thiourea.

$C_{14}H_{19}IN_4S_2$ (434.4).

(c) $N^1$-[3-(1H-Imidazol-4-yl)propyl]-$N^2$-[2-[N-(pyridin-2-yl)-N-(thiophen-2-yl-methyl)amino]ethyl]-guanidine hydriodide 1.00 g (2.3 mmol) of S-methyl-N-[2-[N-(pyridin-2-yl)-N-(thiophen-2-yl-methyl)amino]ethyl]-isothiuronium iodide are reacted with 0.29 g (2.3 mmol) of 3-(1H-imidazol-4-yl)propylamine by a method analogous to that of Example 1(c). The crude product is purified by chromatography on silica gel with ethyl acetate/methanol (80:20). 0.31 g (26%) of the title compound is obtained in the form of a colourless, amorphous solid.

$C_{19}H_{26}IN_7S$ (511.4).

| $^1$H-NMR data: (CD$_3$OD, TMS as internal standard) | δ = 1.8–2.1 (m) 2 H, 2.7 (t) 2 H, 3.2–3.9 (m) 6 H, 4.8 (broad) 5 H, replaceable by D$_2$O, 4.9 (s) 2 H, |
|---|---|

| -continued |
| --- |
| 6.6–7.8 (m) 8 H, |
| 8.2 (dd) 1 H ppm. |

EXAMPLE 5

N$^1$-[3-(1H-Imidazol-4-yl)propyl]-N$^2$-[2-[N-phenyl-N-(thiophen-2-yl-methyl)amino]ethyl]-guanidine

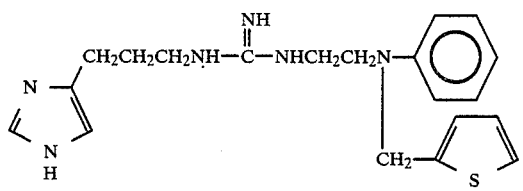

(a) N$^1$-Benzoyl-N$^2$-[2-[N-phenyl-N-(thiophen-2-yl-methyl)amino]-ethyl]-thiourea Prepared by a method analogous to that of Example 1(a) from 7.13 g (31 mmol) of N-phenyl-N-(thiophen-2-yl-methyl)ethylenediamine and 5.00 g (31 mmol) of benzoyl isothiocyanate. 10.64 g (88%) of colourless crystals, melting point 108°–109° C.

C$_{21}$H$_{21}$N$_3$OS$_2$ (395.5).

(b) S-Methyl-N-[2-[N-phenyl-N-(thiophen-2-yl-methyl)amino]-ethyl]-isothiuronium iodide Obtained by a method analogous to that of Example 1(b) from 8.0 g (20 mmol) of N$^1$-benzoyl-N$^2$-[2-[N-phenyl-N-(thiophen-2-yl-methyl)amino]ethyl]-thiourea. 8.0 g (92%) of beige crystals, melting point 127°–128° C., from acetone/diethylether.

C$_{15}$H$_{20}$IN$_3$S$_2$ (433.4).

(c) N$^1$-[3-(1H-Imidazol-4-yl)propyl]-N$^2$-[2-[N-phenyl-N-(thiophen-2-yl-methyl)amino]ethyl]-guanidine From 1.00 g (2.3 mmol) of S-methyl-N-[2-[N-phenyl-N-(thiophen-2-yl-methyl)amino]ethyl]-isothiuronium iodide and 0.30 g (2.4 mmol) of 3-(1H-imidazol-4-yl)-propylamine. 0.35 g (40%) of a colourless, amouphos solid after chromatographic purification on aluminium oxide (neutral) with ethanol/ethyl acetate (1:1) as solvent.

C$_{20}$H$_{26}$N$_6$S (382.5).

| $^1$H-NMR data: (CD$_3$OD, TMS as internal standard) | δ = 1.6–2.0 (m) 2 H, |
| --- | --- |
| | 2.6 (t) 2 H, |
| | 3.2 (t) 2 H, |
| | 3.4–3.7 (m) 4 H, |
| | 4.7 (s) 2 H, |
| | 5.3 (broad) 4 H, replaceable by D$_2$O), |
| | 6.6–7.4 (m) 9 H, |
| | 7.6 (s) 1 H ppm. |

EXAMPLE 6

N$^1$-[3-(1H-Imidazol-4-yl)propyl]-N$^2$-[3(pyridin-2-yl-amino)propyl]-guanidine hydriodide

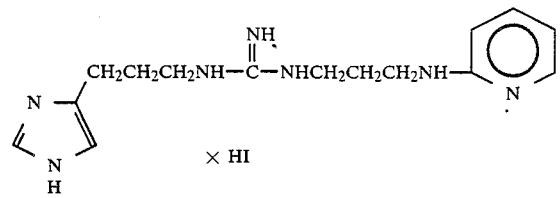

(a) N$^1$-Benzoyl-N$^2$-[3-(pyridin-2-yl-amino)-propyl]-thiourea Obtained by a method analogous to that of Example 1(a) from 1.0 g (6.6 mmol) of N-(pyridin-2-yl)-1,3-propane diamine and 1.1 g (6.6 mmol) of benzoyl isothiocyanate. 2.0 g (96%) of colourless crystals, melting point 111° C., after recrystallisation from ethyl acetate.

C$_{16}$H$_{18}$N$_4$OS (314.4).

(b) S-Methyl-N-[3-(pyridin-2-yl-amino)propyl]-isothiuronium iodide 1.1 g (55%) of a colourless, highly viscous oil are obtained by a method analogous to that of Example 1(b) from 1.8 g (5.7 mmol) of N$^1$-benzoyl-N$^2$-[3-(pyridin-2-yl-amino)-propyl]-thiourea.

C$_{10}$H$_{17}$IN$_4$S (352.2).

(c) N$^1$-[3-(1H-Imidazol-4-yl)propyl]-N$^2$-[3-(pyridin-2-yl-amino)propyl]-guanidine hydriodide 1.00 g (2.8 mmol) of S-methyl-N-[3-(pyridin-2-yl-amino) propyl]-isothiuronium iodide and 0.36 g (2.8 mmol) of 3-(1H-imidazol-4-yl)-propylamine are boiled in 30 ml of acetonitrile for 3 hours. The crude product obtained after removal of the solvent by evaporation under vacuum is chromatographed on silica gel with ethyl acetate/methanol/conc.ammonia (80:19:1). 0.64 g (53%) of a pale yellow, amorphous solid is obtained from the main fraction.

C$_{15}$H$_{24}$IN$_7$ (429.3).

| $^1$H-NMR data: (CD$_3$OD, TMS as internal standard) | δ = 1.7–2.1 (m) 4 H, |
| --- | --- |
| | 2.7 (t) 2 H, |
| | 3.1–3.5 (m) 6 H, |
| | 4.9 (broad) 6 H, replaceable by D$_2$O. |
| | 6.5–6.7 (m) 2 H, |
| | 6.9 (s) 1 H, |
| | 7.3–7.5 (m) 1 H, |
| | 7.6 (s) 1 H, |
| | 7.9 (dd) 1 H ppm. |

EXAMPLE 7

$N^1$-[3-(1H-Imidazol-4-yl)propyl]-$N^2$-[3-[N-phenyl-N-(pyridin-2-yl)amino]propyl]-guanidine hydriodide

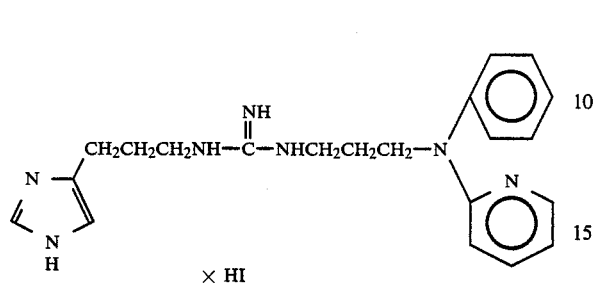

(a) $N^1$-Benzoyl-$N^2$-[3-[N-phenyl-N-(pyridin-2-yl)-amino]propyl]-thiourea 3.7 g (69%) of colourless crystals melting at 124°–126° C. (from methanol) are obtained by a method analogous to that of Example 1 a) from 3.1 g (13.7 mmol) of N-phenyl-N-(pyridin-2-yl)-1,3-propanediamine and 2.2 g (13.7 mmol) of benzoyl isothiocyanate.

$C_{22}H_{22}N_4OS$ (390.5).

(b) S-Methyl-N-[3-[N-phenyl-N-(pyridin-2-yl)-amino]propyl]isothiuronium iodide

Obtained by a method analogous to that of Example 1 (b) from 2.70 g (6.9 mmol) of $N^1$-benzoyl-$N^2$-[3-[N-phenyl-N-(pyridin-2-yl)-amino]-propyl]-thiourea. 2.61 g (88%) of colourless crystals, melting point 130°–131° C., after recrystallization from ethyl acetate.

$C_{16}H_{21}IN_4S$ (428.3)

(c) $N^1$-[3-(1H-Imidazol-4-yl)propyl]-$N^2$-[3-[N-phenyl-N-(pyridin-2-yl)-amino]propyl]-guanidine hydriodide Prepared by a method analogous to that of Example 6 (c) from 1.00 g (2.3 mmol) of S-methyl-N-[3-[N-phenyl-N-(pyridin-2-yl)-amino]propyl]-isothiuronium iodide and 0.29 g (2.3 mmol) of 3-(1H-imidazol-4-yl)-propylamine. 0.78 g (67%) of a colourless, amorphous solid.

$C_{21}H_{28}IN_7$ (505.4).

| $^1$H-NMR data: (CD$_3$OD, TMS as internal standard) | δ = 1.7–2.1 (m) 4 H 2.7 (t) 2 H. 3.1–3.4 (m) 4 H, 4.0 (t) 2 H, 4.8 (broad) 5 H, replaceable by D$_2$O, 6.3–6.8 (m) 2 H, 6.9 (s) 1 H, 7.2–7.7 (m) 7 H, 8.1 (dd) 1 H ppm. |
|---|---|

EXAMPLE 8

$N^1$-[3-(1H-Imidazol-4-yl)propyl]-$N^2$-(3,3-diphenyl-butyl)-guanidine hydrochloride

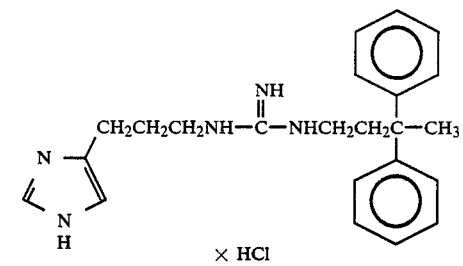

(a) $N^1$-Benzoyl-$N^2$-[3-1H-imidazol-4-yl)propyl]-$N^3$-(3,3-diphenylbutyl)-guanidine

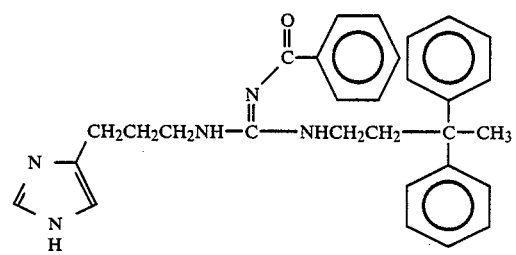

0.70 g (3.1 mmol) of 3,3-Diphenyl-butylamine and 1.08 g (3.1 mmol) of O-phenyl-$N^1$-benzoyl-$N^2$-[3-(1H-imidazol-4-yl) propyl]-isourea are boiled under reflux in 10 ml of ethanol for 15 hours. The solution is concentrated by evaporation under vacuum and the residue obtained is chromatographed on silica gel with dichloromethane/methanol (9:1) as solvent. After evaporation under vacuum, the main fraction yields 1.05 g (71%) of a colourless, amorphous solid.

$C_{30}H_{33}N_5O$ (479.6).

(b) $N^1$-[3-(1H-Imidazol-4-yl)propyl]-$N^2$-(3,3-diphenylbutyl)-guanidine hydrochloride 1.00 g (2.1 mmol) of $N^1$-benzoyl-$N^2$-[3-(1H-imidazol-4-yl) propyl]-$N^3$-(3,3-diphenylbutyl)-guanidine are boiled under reflux with 20 ml of conc. hydrochloric acid for 20 hours. After the reaction mixture has been highly concentrated by evaporation under vacuum, the residue is diluted with 30 ml of water. The solution is extracted 5 times with 20 ml portions of diethylether. The aqueous phase is then filtered and concentrated by evaporation under vacuum at temperatures of up to 50° C. and the residue is concentrated twice by evaporation with 10 ml portions of absolute ethanol. The crude product obtained is chromatographed on silica gel with dichloromethane/methanol (80:20) as solvent. After concentration by evaporation under vacuum, the main fraction yields 0.53 g (61%) of a colourless, amorphous solid.

$C_{23}H_{30}ClN_5$ (412.0).

| $^1$H-NMR data: (CD$_3$OD, TMS as internal standard) | δ = 1.7 (s) 3 H, 1.7–2.0 (m) 2 H, 2.3–2.8 (m) 4 H, 2.9–3.4 (m) 4 H, 4.8 (broad) 5 H, replaceable by D$_2$O, 6.95 (s) 1 H. |
|---|---|

-continued

| | |
|---|---|
| | 7.1–7.4 (m) 10 H, |
| | 7.9 (s) 1 H ppm. |

EXAMPLE 9

$N^1$-[3-(1H-Imidazol-4-yl)propyl]-$N^2$-[3-(4-fluorophenyl)-3-phenyl-butyl-guanidine hydriodide

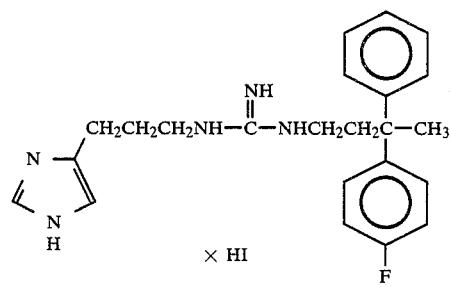

(a) $N^1$-Benzoyl-$N^2$-[3-(4-fluorophenyl)-3-phenyl-butyl]-thiourea

Obtained from 0.54 g (2.2 mmol) of 3-(4-fluorophenyl)-3-phenyl-butylamine and 0.36 g (2.2 mmol) of benzoyl isothiocyanate by a method analogous to that of Example 1 (a). The crude product is used for further reactions without further purification.

$C_{24}H_{23}FN_2OS$ (406.5).

(b) S-Methyl-N-[3-(4-fluorophenyl)-3-phenyl-butyl]-isothiuronium iodide

Prepared by the method of Example 1 (b) from 0.90 g (2.2 mmol) of $N^1$-benzoyl-$N^2$-[3-(4-fluorophenyl)-3-phenyl-butyl]-thiourea. 0.92 g (95%) of a yellowish, amorphous solid.

$C_{18}H_{22}FIN_2S$ (444.3).

(c) $N^1$-[3-(1H-Imidazol-4-yl)propyl]-$N^2$-[3-(4-fluorophenyl)-3-phenyl-butyl]-guanidine hydriodide 0.92 g (2.1 mmol) of S-Methyl-N-[3-(4-fluorophenyl)-3-phenyl-butyl]-isothiuronium iodide and 0.28 g (2.2 mmol) of 3-(1H-imidazol-4-yl)-propylamine are boiled in 10 ml of acetonitrile for 3 hours. Chromatographic purification of the crude product on silica gel with dichloromethane/methanol (80:20) as solvent yields 0.70 g (64%) of a pale yellow, amorphous solid.

$C_{23}H_{29}FIN_5$ (521.4).

| $^1$H-NMR data: | δ = 1.7 (s) 3 H, |
|---|---|
| (CD$_3$OD, TMS as | 1.7–2.1 (m) 2 H, |
| internal standard) | 2.3–2.8 (m) 4 H, |
| | 2.9–3.4 (m) 4 H, |
| | 4.8 (broad) 5 H, replaceable by D$_2$O, |
| | 6.9–7.5 (m) 10 H, |
| | 7.7 (s) 1 H ppm. |

EXAMPLE 10

$N^1$-[3-(1H-Imidazol-4-yl)propyl]-$N^2$-[3,3-bis-(4-fluorophenyl)-butyl]-guanidine hydriodide

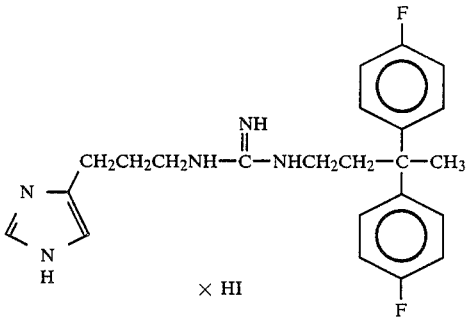

(a) $N^1$-Benzoyl-$N^2$-[3,3-bis-(4-fluorophenyl)-butyl]-thiourea

Prepared from 2.4 g (9 mmol) of 3,3-bis-(4-fluorophenyl)-butylamine and 1.5 g (9 mmol) of benzoylisothiocyanate by the method of Example 1 (a). 3.3 g (85%) of an orange-yellow oil after chromatographic purification on silica gel with dichloromethane as solvent.

$C_{24}H_{22}F_2N_2OS$ (424.5).

(b) S-Methyl-N-[3,3-bis-(4-fluorophenyl)-butyl]-isothiuronium iodide 2.55 g (71%) of the title compound in the form of an orange-yellow, amorphous solid is obtained by a method analogous to that of Example 1 (b) from 3.3 g (7.8 mmol) of $N^1$-benzoyl-$N^2$-[3,3-bis-(4-fluorophenyl)-butyl]-thiourea.

$C_{18}H_{21}F_2IN_2S$ (462.3).

(c) $N^1$-[3-(1H-Imidazol-4-yl)propyl]-$N^2$-[3,3-bis-(4-fluorophenyl)-butyl]-guanidine hydriodide Prepared by a method analogous to that of Example 1 (c) from 2.55 g (5.5 mmol) of S-methyl-N-[3,3-bis-(4-fluorophenyl)-butyl]-isothiuronium iodide and 0.70 g (5.6 mmol) of 3-(1H-imidazol-4-yl)-propylamine. 1.61 g (54%) of a yellow, amorphous solid is obtained.

$C_{23}H_{28}F_2IN_5$ (539.4).

| $^1$H-NMR data: | δ = 1.7 (s) 3 H, |
|---|---|
| (CD$_3$OD, TMS as | 1.7–2.1 (m) 2 H, |
| internal standard) | 2.4–2.9 (m) 4 H, |
| | 3.0–3.4 (m) 4 H, |
| | 4.9 (broad) 5 H, replaceable by D$_2$O, |
| | 6.9–7.4 (m) 9 H, |
| | 8.1 (s) 1 H ppm. |

EXAMPLE 11

N¹-[3-(1H-Imidazol-4-yl)propyl]-N²-[3-(4-fluorophenyl)-3-(5-bromo-3-methyl-pyridin-2-yl)-propyl]-guanidine hydriodide

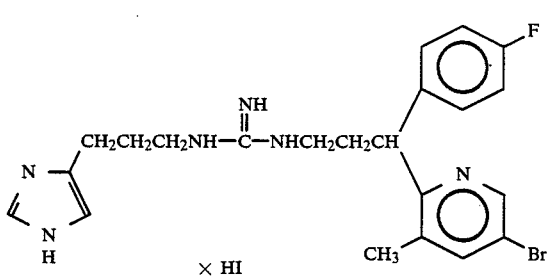

(a) N¹-Benzoyl-N²-[3-(4-fluorophenyl)-3-(5-bromo-3-methyl-pyridin-2-yl)-propyl]-thiourea Prepared from 0.78 g (2.4 mmol) of 3-(4-fluorophenyl)-3-(5-bromo-3-methyl-pyridin-2-yl)-propylamine and 0.39 g (2.4 mmol) of benzoyl isothiocyanate by a method analogous to that of Example 1 (a). The crude product is purified chromatographically on silica gel with dichloromethane as solvent and yields 1.01 g (86%) of a pale yellow, highly viscous oil.

$C_{23}H_{21}BrFN_3OS$ (486.4).

(b) S-Methyl-N-[3-(4-fluorophenyl)-3-(5-bromo-3-methyl-pyridin-2-yl)propyl]-isothiuronium iodide 0.95 g (91%) of a colourless, non-crystalline solid is obtained by a method analogous to that of Example 1 (b) from 1.00 g (2 mmol) of N¹-benzoyl-N²-[3-(4-fluorophenyl)-3-(5-bromo-3-methyl-pyridin-2-yl)propyl]-thiourea.

$C_{17}H_{20}BrFIN_3S$ (524.2).

(c) N¹-[3-(1H-Imidazol-4-yl)propyl]-N²-[3-(4-fluorophenyl)-3-(5-bromo-3-methyl-pyridin-2-yl)-propyl]-guanidine hydriodide 0.70 g (1.33 mmol) of S-methyl-N-[3-(4-fluorophenyl)-3-(5-bromo-3-methyl-pyridin-2-yl)propyl]-isothiuronium iodide and 0.18 g (1.43 mmol) of 3-(1H-imidazol-4-yl)-propylamine are boiled under reflux in 10 ml of n-butanol for 3 hours. The solvent is evaporated off under vacuum and the brown crude product obtained is chromatographically purified on silica gel with ethyl acetate/ethanol (60:40) as solvent. 0.48 g (60%) of a colourless, amorphous solid is obtained.

$C_{22}H_{27}BrFIN_6$ (601.3).

| ¹H-NMR data: (CD₃OD, TMS as internal standard) | δ = 1.7–2.9 (m) 6 H, 2.3 (s) 3 H, 3.1–3.5 (m) 4 H, 4.5 (t) 1H, 5.0 (broad) 5 H, replaceable by D₂O, 7.0–7.6 (m) 5 H, 7.8 (s) 1 H, 7.9 (d) 1 H, 8.7 (d) 1 H ppm. |
|---|---|

EXAMPLE 12

N¹-[2-(5-Methyl-1H-imidazol-4-yl)ethyl]-N²-[3-(4-fluorophenyl)-3-(pyridin-2-yl)propyl]-guanidine

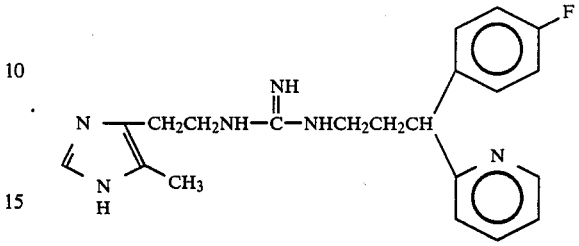

(a) N¹-Benzoyl-N²-[3-(4-fluorophenyl)-3-(pyridin-2-yl)propyl]-thiourea

Prepared by a method analogous to that of Example 1 (a) from 11.5 g (50 mmol) of 3-(4-fluorophenyl)-3-(pyridin-2-yl)-propylamine and 8.2 g (50 mmol) of benzoyl isothiocyanate in chloroform.18.1 g (92%) of colourless crystals, melting point 94°–96° C., after recrystallisation from i-propanol.

$C_{22}H_{20}FN_3OS$ (393.5).

(b) S-Methyl-N-[3-(4-fluorophenyl)-3-(pyridin-2-yl)propyl]-isothiuronium iodide 10.4 g (80%) of a colourless, amorphous solid are obtained by a method analogous to that of Example 1 (b) from 11.8 g (30 mmol) of N¹-benzoyl-N²-[3-(4-fluorophenyl)-3-(pyridin-2-yl)propyl]-thiourea. After repeated stirring up with diethylether, the solid product obtained melts at 80° C. but not with a sharp melting point.

$C_{16}H_{19}FIN_3S$ (431.3).

(c) N¹-[2-(5-Methyl-1H-imidazol-4-yl)ethyl]-N²-[3-(4-fluorophenyl)-3-(pyridin-2-yl)propyl]-guanidine 1.38 g (3.2 mmol) of S-methyl-N-[3-(4-fluorophenyl)-3-(pyridin-2-yl)propyl]-isothiuronium iodide and 0.40 g (3.2 mmol) of 2-(5-methyl-1H-imidazol-4-yl)-ethylamine are boiled under reflux in 20 ml of acetonitrile for 3 hours. After removal of the solvent by evaporation under vacuum, the crude product is chromatographed on silica gel with ethyl acetate/methanol/conc.ammonia (50:47:3) as solvent. After concentration by evaporation under vacuum, the main fraction yields 0.40 g (33%) of a yellowish, amorphous solid.

$C_{21}H_{25}FN_6$ (380.5)

| ¹H-NMR data: (CD₃OD, TMS as internal standard) | δ = 2.2 (s) 3 H, 2.2–2.6 (m) 2 H, 2.8 (t) 2 H, 3.1–3.6 (m) 4 H, 5.0 (broad) 4 H, replaceable by D₂O, 6.9–8.0 (m) 8 H, 8.6 (dd) 1 H ppm. |
|---|---|

EXAMPLE 13

N¹[3-(1H-Imidazol-4-yl)propyl]-N²-[2-(diphenylmethoxy)-ethyl]-guanidine hydriodide

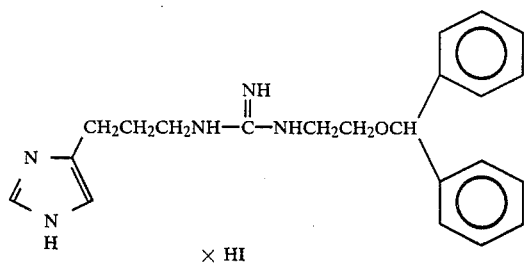

(a) N¹-Benzoyl-N²-[2-(diphenylmethoxy)ethyl]-thiourea 7.8 g (34 mmol) of 2-(diphenylmethoxy)-ethylamine and 5.6 g (34 mmol) of benzoylisothiocyanate are stirred up in 60 ml of ethyl acetate for 2 hours at room temperature. The solid which precipitates is suction filtered, washed with ethyl acetate and recrystallised from ethanol. 11.1 g (83%) of colourless crystals melting at 126° to 127° C. are obtained.

$C_{23}H_{22}N_2O_2S$ (390.5).

(b) S-Methyl-N-[2-(diphenylmethoxy)ethyl]-isothiuronium iodide

Prepared by a method analogous to that of Example 1 (b) from 11.1 g (28 mmol) of N¹-benzoyl-N²-[2-(diphenylmethoxy) ethyl]-thiourea. 11.4 g (94%) of a colourless, highly viscous oil are obtained.

$C_{17}H_{21}IN_2OS$ (428.3)

(c) N¹-[3-(1H-Imidazol-4-yl)propyl]-N²-[2-(diphenylmethoxy) ethyl]-guanidine hydriodide Prepared by a method analogous to that of Example 1 (c) from 1.73 g (4 mmol) of S-methyl-N-[2-(diphenylmethoxy) ethyl]-isothiuronium iodide and 0.50 g (4 mmol) of 3-(1H-imidazol-4-yl)-propylamine. 1.41 g (70%) of a colourless amorphous solid after chromatographic purification on silica gel with dichloromethane/methanol (80:20) as solvent.

$C_{22}H_{28}IN_5O$ (505.4).

| ¹H-NMR data: (CD₃OD, TMS as internal standard) | $\delta =$ 1.7–2.1 (m) 2 H, 2.7 (t) 2 H, 3.1–3.8 (m) 6 H, 4.9 (broad) 5 H, replaceable by D₂O, 5.6 (s) 1 H, 7.0 (s) 1 H, 7.2–7.6 (m) 10 H, 8.0 (s) 1 H, ppm. |
|---|---|

EXAMPLE 14

N¹-[3-(3,4-Dichlorophenyl)-3-(pyridin-2-yl)propyl]-N²-[3-(1H-imidazol-4-yl)propyl]-guanidine

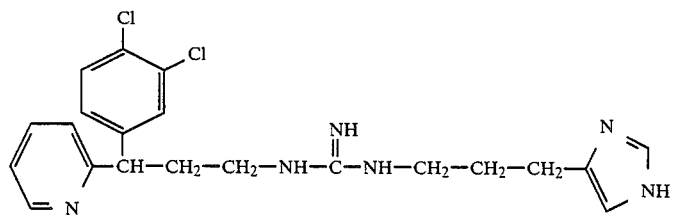

(a) N¹-Benzoyl-N²-[3-(3,4-dichlorophenyl)-3-(pyridin-2-yl) propyl]-N³-[3-(1H-imidazol-4-yl)propyl]-guanidine 1.41 g (5 mmol) of 3-(3,4-dichlorophenyl)-3-(pyridin-2-yl)-propylamine and 1.59 g (5 mmol) of N-benzoyl-diphenyl-imidocarbonate are stirred up in 20 ml of methylene chloride at room temperature for 20 minutes. The solvent is then distilled off under vacuum, the oily residue is taken up with 30 ml of pyridine, and after the addition of 0.65 g (5.2 mmol) of 3-(1H-imidazol-4-yl)-propylamine the reaction mixture is heated to 100° C. for 45 minutes. The reaction mixture is then concentrated by evaporation under vacuum and the residue is taken up in 5% hydrochloric acid and extracted with ether. The extract is then made alkaline with ammonia and extracted by shaking with methylene chloride, and the organic phase is washed with water, dehydrated over sodium sulphate and concentrated by evaporation under vacuum. The reaction product is isolated and purified by layer chromatography on gypsum-containing silica gel 60 PF₂₅₄ (solvent: chloroform/methanol 99.5/0.5; ammoniacal atmosphere). After concentration of the eluates by evaporation, 1.35 g (50%) of a colourless, amorphous solid (foam) are obtained.

$C_{28}H_{28}Cl_2N_6O$ (535.5).

| ¹H-NMR data: (CDCl₃, TMS as internal standard) | $\delta =$ 1.94 (m) 2 H, 2.25 (broad) 1 H, 2.5–2.8 (m) 3H, 3.3 (broad) 2 H, 3.5 (broad) 1 H, 3.9 (broad) 1 H, 4.14 (dd) 1 H, 6.73 (s) 1 H, 6.9–7.8 (m) 10 H, 8.11 (d) 2 H, 8.56 (d) 1 H, 10.2–10.9 (broad) 1 H, replaceable by D₂O, ppm. |
|---|---|

(b) N¹-[3-(3,4-Dichlorophenyl)-3-(pyridin-2-yl)propyl]-N²-[3-(1H-imidazol-4-yl)propyl]-guanidine 0.8 g (1.5 mmol) of N¹-benzoyl-N²-[3-(3,4-dichlorophenyl)-3-(pyridin-2-yl)propyl]-N³-[3-(1H-imidazol-4-yl)propyl]-guanidine are heated under reflux in 40 ml of 20% hydrochloric acid for 10 hours. The hydrochloric acid solution is then extracted three times with ether, evaporated to dryness under vacuum and dried in a high vacuum. 0.74 g (91%) of the trihydrochloride is left behind as a hygroscopic, amorphous solid.

$C_{21}H_{24}Cl_2N_6 \times 3HCl$ (540.8).

MS (FAB method): m/z (rel. Int. [%])=431 ([M+H]⁺, 35), 264 (80), 109 (100).

| | | |
|---|---|---|
| 1H-NMR data: (DMSO-d6, TMS as internal standard) | δ = | 1.84 (m) 2 H, 2.3–2.65 (m) 2 H, 2.72 (t) 2 H, 3.0–3.35 (m) 4 H, 4.72 (t) 1 H, 7.45–8.2 (m) 10 H, 4 H replaceable by D2O, 8.28 (dd) 1 H, 8.73 (d) 1 H, 9.05 (s) 1 H, 14.45 (broad) 1 H, replaceable by D2O, 14.8 (broad) 1 H, replaceable by D2O, ppm. |

EXAMPLE 15

$N^1$-[3-(3,5-Dichlorophenyl)-3-(pyridin-2-yl)propyl]-$N^2$-[3-(1H-imidazol-4-yl)propyl]-guanidine

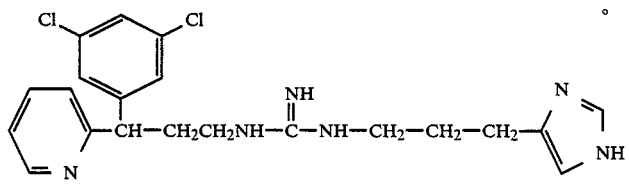

(a) $N^1$-Benzoyl-$N^2$-[3-(3,5-dichlorophenyl)-3-(pyridin-2-yl) propyl-$N^3$-[3-(1H-imidazol-4-yl)propyl]-guanidine The method of preparation and isolation is analogous to that of Example 14 (a), starting from 1.41 g (5 mmol) of 3-(3,5-dichlorophenyl)-3-(pyridin-2-yl)-propylamine. Yield: 1.25 g (47%) of a colourless, amorphous solid (foam)

$C_{28}H_{28}Cl_2N_6O$ (535.5).

| | | |
|---|---|---|
| 1H-NMR data: (CDCl3, TMS as internal standard) | δ = | 1.95 (m) 2 H, 2.3 (broad) 1 H, 2.55–2.8 (m) 3 H, 3.3 (broad) 2 H, 3.5 (broad) 1 H, 3.85 (broad) 1 H, 4.12 (dd) 1 H, 6.73 (s) 1 H, 6.9–7.75 (m) 10 H, 8.12 (d) 2 H, 8.57 (d) 1 H, 10.2–10.9 (broad) 1 H, replaceable by D2O, ppm. |

(b) $N^1$-[3-(3,5-Dichlorophenyl)-3-(pyridin-2-yl)propyl]-$N^2$-[3-(1H-imidazol-4-yl)propyl]-guanidine The method of preparation is analogous to that of Example 14 (b) starting from 0.8 g (1.5 mmol) of $N^1$-benzoyl-$N^2$-[3-(3,5-dichlorophenyl)-3-(pyridin-2-yl)propyl]-$N^3$-[3-(1H-imidazol-4-yl)propyl]-guanidine.

Yield: 0.7 g (86%) of the trihydrochloride in the form of a hygroscopic, amorphous solid.

$C_{21}H_{24}Cl_2N_6 \times 3$ HCl (540.8).

MS (FAB method): m/z (rel. Int. [%])=431 ([M+H]+, 24), 264 (72), 201 (28), 109 (100).

| | | |
|---|---|---|
| 1H-NMR data: (DMSO-d6, TMS as internal standard) | δ = | 1.83 (m) 2 H, 2.3–2.65 (m) 2 H, 2.71 (t) 2 H, 3.17 (dt) 2 H, 3.44 (dt) 2 H, 4.60 (t) 1 H, 7.5–8.2 (m) 11 H, 4 H, replaceable by D2O, 8.68 (d) 1 H, 9.04 (d) 1 H, 14.35 (broad) 1 H, replaceable by D2O, 14.7 (broad) 1 H, replaceable by D2O, ppm. |

EXAMPLE 16

$N^1$-[3-(2,4-Dichlorophenyl)-3-(pyridin-2-yl)propyl]-$N^2$-[3-(1H-imidazol-4-yl)-propyl]-guanidine

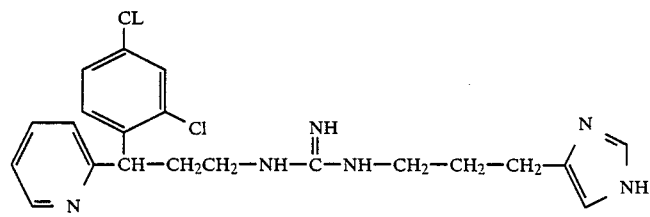

(a) $N^1$-Benzoyl-$N^2$-[3-(2,4-dichlorophenyl)-3-(pyridin-2-yl) propyl-$N^3$-[3-(1H-imidazol-4-yl)-propyl]-guanidine The method of preparation is analogous to that of Example 14 (a), starting from 1.41 g (5 mmol) of 3-(2,4-dichlorophenyl)-3-(pyridin-2-yl)-propylamine.

Yield: 1.1 g (41%) of a colourless, amorphous solid (foam).

$C_{28}H_{28}Cl_2N_6O$ (535.5).

| | | |
|---|---|---|
| 1H-NMR data: (CDCl3, TMS as internal standard) | δ = | 1.95 (m) 2 H, 2.25 (broad) 1 H, 2.5–2.85 (m) 3 H, 3.1–3.7 (broad) 3 H, 3.9 (broad) 1 H, 4.72 (m) 1 H, 6.7–7.8 (m) 11 H, 8.12 (d) 2 H, 8.59 (d) 1 H, 10.3–11.0 (broad) 1 H, replaceable by D2O, ppm. |

(b) $N^1$-[3-(2,4-Dichlorophenyl)-3-(pyridin-2-yl)propyl]-$N^2$-[3-(1H-imidazol-4-yl)propyl]-guanidine The method of preparation is analogous to that of Example 14 (b) starting from 0.65 g (1.2 mmol) of $N^1$-benzoyl-$N^2$-[3-(2,4-dichlorophenyl)-3-(pyridin-2-yl)-propyl-$N^3$-[3-(1H-imidazol-4-yl)propyl]-guanidine.

Yield: 0.6 g (92%) of the trihydrochloride in the form of a hygroscopic, amorphous solid.

$C_{21}H_{24}Cl_2N_6 \times 3$ HCl (540.8).

MS (FAB method): m/z (rel. Int. [%])=431 ([M+H]+, 49), 264 (82), 237 (12), 201 (24), 167 (20), 126 (15), 118 (13), 109 (100), 100 (59).

| $^1$H-NMR data: (DMSO-d$_6$, TMS as internal standard) | $\delta =$ | 1.85 (m) 2 H, 2.36 (m) 1 H, 2.53 (m) 1 H, 2.73 (t) 2 H, 3.18 (m) 4 H, 4.93 (t) 1 H, 7.49 (s) 1 H, 7.50 (d) 1 H, 7.6–7.8 (m) 6 H, 2 H replaceable by D$_2$O, 8.03 (m) 1 H replaceable by D$_2$O, 8.07 (m) 1 H, replaceable by D$_2$O, 8.19 (dd) 1 H, 8.74 (d) 1 H, 9.06 (s) 1 H, 14.5 (broad) 1 H, replaceable by D$_2$O, 14.85 (broad) 1 H, replaceable by D$_2$O, ppm. |
|---|---|---|

EXAMPLE 17

$N^1$-[3-(3,4-Difluorophenyl)-3-(pyridin-2-yl)propyl]-$N^2$-[3-(1H-imidazol-4-yl)propyl]-guanidine

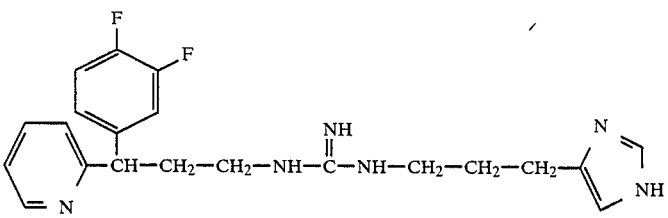

(a) $N^1$-Benzoyl-$N^2$-[3-(3,4-difluorophenyl)-3-(pyridin-2-yl)propyl-$N^3$-[3-(1H-imidazol-4-yl)propyl]-guanidine The method of preparation is analogous to that of Example 14 (a), starting from 1.24 g (5 mmol) of 3-(3,4-difluorophenyl)-3-(pyridin-2-yl)-propylamine.

Yield: 1.2 g (48%) of a colourless, amorphous solid (foam).

$C_{28}H_{28}F_2N_6O$ (502.6)

| $^1$H-NMR data: (CDCl$_3$, TMS as internal standard) | | 1.95 (m) 2 H, 2.3 (broad) 1 H, 2.55–2.8 (m) 3 H, 3.32 (broad) 2 H, 3.5 (broad) 1 H, 3.85 (broad) 1 H, 4.15 (dd) 1 H, 6.73 (s) 1 H, 6.8–7.75 (m) 10 H, 8.12 (d) 2 H, 8.57 (d) 1 H, 10.2–10.9 (broad) 1 H, replaceable by D$_2$O, ppm. |
|---|---|---|

(b) $N^1$-[3-(3,4-Difluorophenyl)-3-(pyridin-2-yl)propyl]-$N^2$-[3-(1H-imidazol-4-yl)propyl]-guanidine The method of preparation is analogous to that of Example 14 (b), starting from 0.76 g (1.5 mmol) of $N^1$-benzoyl-$N^2$-[3-(3,4-difluorophenyl)-3-(pyridin-2-yl)propyl]-$N^3$-[3-(1H-imidazol-4-yl)propyl]-guanidine.

Yield: 0.68 g (89%) of the trihydrochloride in the form of a hygroscopic, amorphous solid.

$C_{21}H_{24}F_2N_6 \times 3$ HCl (507.8).

Molar mass: (MS): Calculated: 398.2031. Found: 398.2028.

MS (FAB method): m/z (rel. Int [%])=399 ([M+H]+, 58) 232 (100), 204 (23), 109 (43).

| $^1$H-NMR data: (DMSO-d$_6$, TMS as internal standard) | $\delta =$ | 1.85 (m) 2 H, 2.35–2.65 (m) 2 H, 2.73 (t) 2 H, 3.11 (dt) 2 H, 3.18 (dt) 2 H, 4.73 (t) 1 H, 7.35–7.8 (m) 7 H, 2 H replaceable by D$_2$O, 7.99 (m) 3 H, 2 H replaceable by D$_2$O, 8.31 (dd) 1 H, 8.74 (d) 1 H, 9.05 (s) 1 H, 14.45 (broad) 1 H, replaceable by D$_2$O, ppm 14.8 (broad) 1 H, replaceable by D$_2$O, ppm 14.8 (broad) 1 H, replaceable by D$_2$O, ppm. |
|---|---|---|

EXAMPLE 18

N$^1$-[3-(3,5-Difluorophenyl)-3-(pyridin-2-yl)propyl]-N$^2$-[3-(1H-imidazol-4-yl)propyl]-guanidine

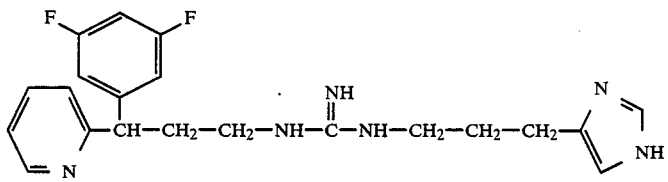

(a) N$^1$-Benzoyl-N$^2$-[3-(3,5-difluorophenyl)-3-(pyridin-2-yl) propyl]-N$^3$-[3-(1H-imidazol-4-yl)propyl]-guanidine The method of preparation is analogous to that of Example 14 (a), starting from 1.24 g of 3-(3,5-difluorophenyl)-3-(pyridin-2-yl)-propylamine.

Yield: 1.3 g (52%) of a colourless, amorphous solid. C$_{28}$H$_{28}$F$_2$N$_6$O (502.6).

| $^1$H-NMR data: (CDCl$_3$, TMS as internal standard) | δ = | 1.96 (m) 2 H, 2.3 (broad) 1 H, 2.6–2.8 (m) 3 H, 3.34 (broad) 2 H, 3.5 (broad) 1 H, 3.9 (broad) 1 H, 4.17 (dd) 1 H, 6.6–7.8 (m) 11 H, 8.12 (d) 2 H, 8.58 (d) 1 H, 10.3–10.9 (broad) 1 H, replaceable by D$_2$O, ppm. |
|---|---|---|

(b) N$^1$-[3-(3,5-difluorophenyl)-3-(pyridin-2-yl)propyl]-N$^2$-[3-(1H-imidazol-4-yl)propyl]-guanidine The method of preparation is analogous to that of Example 14 (b), starting from 0.76 g (1.5 mmol) of N$^1$-benzoyl-N$^2$-[3-(3,5-difluorophenyl)-3-(pyridin-2-yl)propyl]-N$^3$-[3-(1H-imidazol-4-yl)propyl]-guanidine.

Yield: 0.65 g (85%) of the trihydrochloride in the form of a hygroscopic, amorphous solid.

C$_{21}$H$_{24}$F$_2$N$_6$×3 HCl (507.8).

MS (FAB method): m/z (rel. Int. [%])=399 ([M+H]$^+$, 80), 232 (100), 204 (18), 109 (60), 100 (36), 95 (11).

| $^1$H-NMR data: (DMSO-d$_6$, TMS as internal standard) | δ = | 1.85 (m) 2 H, 2.35–2.65 (m) 2 H, 2.72 (t) 2 H, 3.0–3.3 (m) 4 H, 4.78 (t) 1 H, 7.16 (dd) 1 H, 7.36 (d) 2 H, 7.51 (s) 1 H, 7.62 (s) 2 H, replaceable by D$_2$O, 7.76 (dd) 1 H, 8.02 (m) 3 H, 2 H replaceable by D$_2$O, 8.32 (dd) 1 H, 8.75 (d) 1 H, 9.05 (s) 1 H, 14.45 (broad) 1 H, replaceable by D$_2$O, 14.8 (broad) 1 H, replaceable by D$_2$O, ppm. |
|---|---|---|

EXAMPLE 19

N$^1$-[3-(1H-imidazol-4-yl)propyl]-N$^2$-[3-(4-methylphenyl)-3-(pyridin-2-yl)propyl]-guanidine

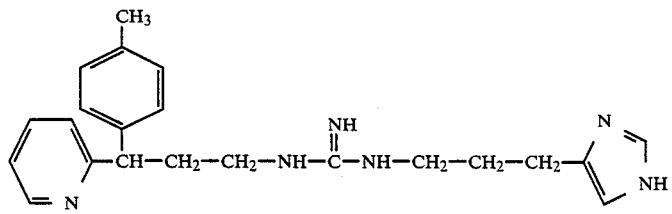

(a) N$^1$-Benzoyl-N$^2$-[3-(1H-imidazol-4-yl)propyl]-N$^3$-[3-(4-methylphenyl)-3-(pyridin-2-yl)propyl]-guanidine The method of preparation is analogous to that of Example 14 (a), starting from 1.13 g (5 mmol) of 3-(4-methylphenyl)-3-(pyridin-2-yl)-propylamine.

Yield: 1.3 g (54%) of a colourless, amorphous solid (foam).

C$_{29}$H$_{32}$N$_6$O (480.6).

| $^1$H-NMR data: (CDCl$_3$, TMS as internal standard) | δ = | 1.96 (m) 2 H, 2.1–2.45 (m) 1 H, 2.30 (s) 3 H, 2.55–2.8 (m) 3 H, 3.17–3.7 (broad) 3 H, 3.9 (broad) 1 H, 4.16 (dd) 1 H, 6.72 (s) 1 H, 7.0–7.7 (m) 11 H, 8.12 (d) 2 H, 8.55 (d) 1 H, 10.75 (broad) 1 H, replaceable by D$_2$O, ppm. |
|---|---|---|

(b) N$^1$-[3-(1H-Imidazol-4-yl)propyl]-N$^2$-[3-(4-methylphenyl)-3-(pyridin-2-yl)propyl]-guanidine The method of preparation is analogous to that of Example 14 (b), starting from 0.72 g (1.5 mmol) of N$^1$-benzoyl-N$^2$-[3-(1H-imidazol-4-yl)propyl]-N$^3$-[3-(4-methylphenyl)-3-(pyridin-2-yl)propyl]-guanidine.

Yield: 0.66 g (90%) of the trihydrochloride in the form of a hygroscopic, amorphous solid.

C$_{22}$H$_{28}$N$_6$×3HCl (485.9).

MS (FAB method): m/z (rel. Int. [%])=377 ([M+H]$^+$, 71), 210 (100), 182 (17), 109 (37), 100 (29).

| | | |
|---|---|---|
| $^1$H-NMR data: (DMSO-d$_6$, TMS as internal standard) | δ = | 1.84 (m) 2 H, 2.2–2.65 (m) 2 H, 2.25 (s) 3 H, 2.72 (t) 2 H, 3.11 (dt) 2 H, 3.18 (dt) 2 H, 4.65 (t) 1 H, 7.16 (d) 2 H, 7.3–8.45 (m) 10 H, 4 H replaceable by D$_2$O, 8.73 (d) 1 H, 9.05 (d) 1 H, 14.45 (broad) 1 H, replaceable by D$_2$O, 14.8 (broad) 1 H, replaceable by D$_2$O, ppm. |

EXAMPLE 20

N$^1$-[3-(3-Chlorophenyl)-3-(pyridin-2-yl)propyl]-N$^2$-[3-(1H-imidazol-4-yl)propyl]-guanidine

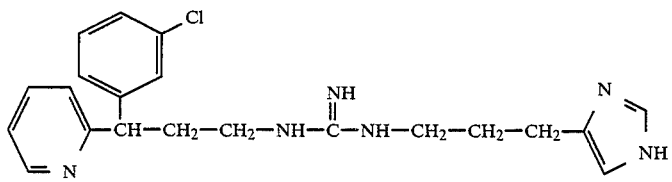

(a) N$^1$-Benzoyl-N$^2$-[3-(3-chlorophenyl)-3-(pyridin-2-yl) propyl]-N$^3$-[3-(1H-imidazol-4-yl)propyl]-guanidine The method of preparation is analogous to that of Example 14 (a), starting from 1.23 g (5 mmol) of 3-(3-chlorophenyl)-3-(pyridin-2-yl)-propylamine.

Yield: 1.45 g (58%) of a colourless, amorphous solid (foam).

C$_{28}$H$_{29}$ClN$_6$O (501.0).

| | | |
|---|---|---|
| $^1$H-NMR data: (CDCl$_3$, TMS as internal standard) | δ = | 1.96 (m) 2 H, 2.32 (broad) 1 H, 2.55–2.75 (m) 1 H, 2.69 (t) 2 H, 3.15–3.7 (broad) 3 H, 3.9 (broad) 1 H, 4.16 (dd) 1 H, 6.73 (s) 1 H, 7.0–7.75 (m) 11 H, 8.12 (d) 2 H, 8.56 (d) 1 H, 10.2–11.0 (broad) 1 H, replaceable by D$_2$O, ppm. |

(b) N$^1$-[3-(3-Chlorophenyl)-3-(pyridin-2-yl)propyl]-N$^2$-[3-(1H-imidazol-4-yl)propyl]-guanidine The method of preparation is analogous to that of Example 14 (b), starting from 0.75 g (1.5 mmol) of N$^1$-benzoyl-N$^2$-[3-(3-chlorophenyl)-3-(pyridin-2-yl)propyl]-N$^3$-[3-(1H-imidazol-4-yl)propyl]-guanidine.

Yield: 0.69 g (91%) of the trihydrochloride in the form of a hygroscopic, amorphous solid.

C$_{21}$H$_{25}$ClN$_6$×3HCl (506.3).

MS (FAB method): m/z (rel. Int. [%])=397 ([M+H]$^+$ 77), 230 (100), 109 (65), 100 (41).

| | | |
|---|---|---|
| $^1$H-NMR data: (DMSO-d$_6$, TMS as internal standard) | δ = | 1.83 (m) 2 H, 2.25–2.65 (m) 2 H, 2.71 (t) 2 H, 3.10 (dt) 2 H, 3.18 (dt) 2 H, 4.64 (t) 1 H, 7.3–7.75 (m) 7 H, 2 H replaceable by D$_2$O, 7.8–8.1 (m) 4 H, 2 H replaceable by D$_2$O, 8.20 (dd) 1 H, 8.70 (d) 1 H, 9.04 (s) 1 H, 14.35 (broad) 1 H, replaceable by D$_2$O, 14.7 (broad) 1 H, replaceable by D$_2$O, ppm. |

EXAMPLE 21

N$^1$-[3-(2-Chlorophenyl)-3-(pyridin-2-yl)propyl]-N$^2$-[3-(1H-imidazol-4-yl)propyl]-guanidine (a) N$^1$-Benzoyl-N$^2$-[3-(2-chlorophenyl)-3-(pyridin-2-yl)propyl]-N$^3$-[3-(1H-imidazol-4-yl)propyl]-guanidine The method of preparation is analogous to that of Example 14 (a), starting from 1.23 g (5 mmol) of 3-(2-chlorophenyl)-3-(pyridin-2-yl)-propylamine.

Yield: 1.1 g (44%) of a colourless, amorphous solid (foam).

C$_{28}$H$_{29}$ClN$_6$O (501.0)

| | | |
|---|---|---|
| $^1$H-NMR-data: (CDCl$_3$, TMS as internal standard) | δ = | 1.97 (m) 2 H, 2.25 (m) 1 H, 2.5–2.7 (m) 3 H, 3.1–3.7 (broad) 3 H, 3.90 (broad) 1 H, 4.73 (m) 1 H, 6.71 (s) 1 H, 6.8–7.9 (m) 11 H, 8.11 (d) 2 H, 8.57 (d) 1 H, 8.2–8.9 (broad) 1 H, replaceable by D$_2$O, ppm. |

(b) $N^1$-[3-(2-Chlorophenyl)-3-(pyridin-2-yl)propyl]-$N^2$-[3-(1H-imidazol-4-yl)propyl]-guanidine The method of preparation is analogous to that of Example 14 (b), starting from 0.55 g (1.1 mmol) of $N^1$-benzoyl-$N^2$-[3-(2-chlorophenyl)-3-(pyridin-2-yl)propyl]-$N^3$-[3-(1H-imidazol-4-yl)propyl]-guanidine.

Yield: 0.49 g (88%) of the trihydrochloride in the form of a hygroscopic, amorphous solid.

$C_{21}H_{25}ClN_6 \times 3$ HCl (506.3).

MS (FAB method): m/z rel. Int. [%] = 397 ([M+H]+, 64), 230 (100), 203 (13), 194 (20), 168 (18), 167 (32), 126 (13), 109 (66), 100 (37), 95 (11).

| $^1$H-NMR data: (DMSO-$d_6$, TMS as internal standard) | $\delta$ = 1.86 (m) 2 H, 2.35–2.7 (m) 2 H, 2.73 (t) 2 H, 3.1–3.4 (m) 4 H, 5.01 (t) 1 H, 7.3–8.0 (m) 9 H, 2 H replaceable by D$_2$O, 8.05 (m) 2 H, replaceable by D$_2$O. 8.24 (dd) 1 H, 8.77 (d) 1 H, 9.06 (s) 1 H, 14.50 (broad) 1 H, replaceable by D$_2$O. 14.83 (broad) 1 H, replaceable by D$_2$O, ppm. |
|---|---|

EXAMPLE 22

$N^1$-[3-(3-Fluorophenyl)-3-(pyridin-2-yl)propyl]-$N^2$-[3-(1H-imidazol-4-yl)propyl]-guanidine

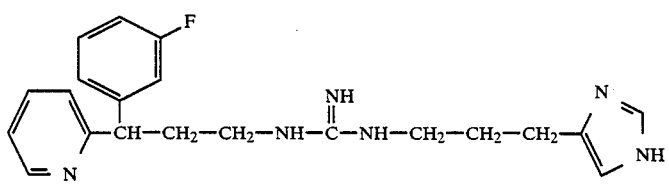

(a) $N^1$-Benzoyl-$N^2$-[3-(3-fluorophenyl)-3-(pyridin-2-yl)propyl]-$N^3$-[3-(1H-imidazol-4-yl)propyl]-guanidine.

The method of preparation is analogous to that of Example 14 (a), starting from 1.15 g (5 mmol) of 3-(3-fluorophenyl)-3-(pyridin-2-yl)-propylamine.

Yield: 1.19 g (49%) of a colourless, amorphous solid (foam).

$C_{28}H_{29}FN_6O$ (484.6)

(b) $N^1$-[3-(3-Fluorophenyl)-3-(pyridin-2-yl)propyl]-$N^2$-[3-(1H-imidazol-4-yl)propyl]-guanidine The method of preparation is analogous to that of Example 14 (b) starting from 0.73 g (1.5 mmol) of $N^1$-benzoyl-$N^2$-[3-(3-fluorophenyl)-3-(pyridin-2-yl)propyl]-$N^3$-[3-(1H-imidazol-4-yl)propyl]-guanidine Yield: 0.65 g (88%) of the trihydrochloride in the form of a hygroscopic, amorphous solid.

$C_{21}H_{25}FN_6 \times 3HCl$ (489.9).

MS (FAB method): m/z (rel. Int. [%]) = 381 ([M+H]+, 47), 214 (100), 186 (23), 109 (49), 100 (24).

| $^1$H-NMR data: (DMSO-$d_6$, TMS as internal standard) | $\delta$ = 1.85 (m) 2 H, 2.35–2.7 (m) 2 H. 2.73 (t) 2 H, 3.05–3.35 (m) 4 H. 4.76 (t) 1 H, 7.10 (m) 1 H, 7.25–7.85 (m) 7 H, 2 H replaceable by D$_2$O, 8.03 (m) 3 H, 2 H replaceable by D$_2$O, 8.35 (dd) 1 H, 8.35 (d) 1 H, 9.05 (s) 1 H, 14.5 (broad) 1 H, repaceable by D$_2$O, 14.85 (broad) 1 H, replaceable by D$_2$O, ppm. |
|---|---|

EXAMPLE 23

$N^1$-[3-(2-Fluorophenyl)-3-(pyridin-2-yl)propyl]-$N^2$-[3-(1H-imidazol-4-yl)propyl]-guanidine

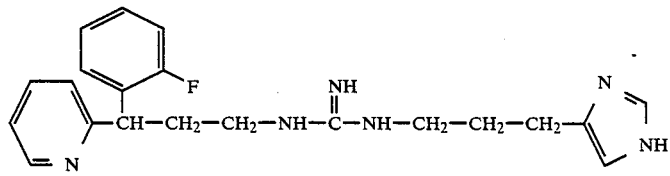

(a) $N^1$-Benzoyl-$N^2$-[3-(2-fluorophenyl)-3-(pyridin-2-yl)propyl]-$N^3$-[3-(1H-imidazol-4-yl)propyl]-guanidine The method of preparation is analogous to that of Example 14 (a), starting from 1.15 g (5 mmol) of 3-(2-fluorophenyl)-3-(pyridin-2-yl)-propylamine.

Yield: 1.24 g (51%) of a colourless, amorphous solid (foam).

$C_{28}H_{29}FN_6O$ (484.6)

(b) $N^1$-[3-(2-Fluorophenyl)-3-(pyridin-2-yl)propyl]-$N^2$-[3-(1H-imidazol-4-yl)propyl]-guanidine The method of preparation is analogous to that of Example 14 (b), starting from 0.73 g (1.5 mmol) of $N^1$-benzoyl-$N^2$-[3-(2-fluorophenyl)-3-(pyridin-2-yl)propyl]-$N^3$-[3-(1H-imidazol-4-yl)propyl]-guanidine.

Yield: 0.66 g (90%) of the trihydrochloride in the form of a hygroscopic, amorphous solid.

$C_{21}H_{25}FN_6 \times 3HCl$ (489.9).

MS (FAB method): m/z (rel. Int. [%]) = 381 ([M+H]+, 61), 214 (100), 186 (11), 109 (50), 100 (32).

| $^1$H-NMR data: (DMSO-$d_6$, TMS as internal standard) | $\delta$ = 1.85 (m) 2 H, 2.37 (m) 1 H, 2.6 (m) 1 H, 2.73 (t) 2 H, 3.18 (m) 4 H, 4.82 (t) 1 H, |
|---|---|

-continued

| | |
|---|---|
| | 7.15–7.45 (m) 3 H, |
| | 7.47 (s) 1 H, |
| | 7.5–7.85 (m) 5 H, 2 H replaceable by D₂O, |
| | 7.95–8.05 (m) 2 H, replaceable by D₂O, |
| | 8.22 (dd) 1 H, |
| | 8.73 (d) 1 H, |
| | 9.04 (s) 1 H, |
| | 14.45 (broad) 1 H, replaceable by D₂O, |
| | 14.80 (broad) 1 H, replaceable by D₂O, ppm. |

EXAMPLE 24

N¹-[3-(4-Fluorophenyl)-3-(pyridin-3-yl)propyl]-N²-[3-(1H-imidazol-4-yl)-propyl]-guanidine

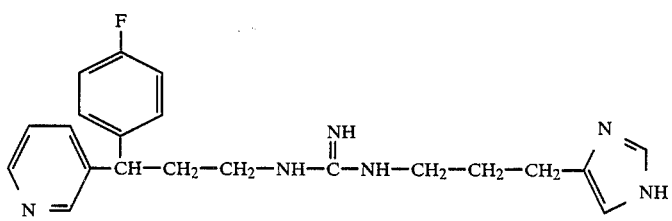

(a) N¹-Benzoyl-N²-[3-(4-fluorophenyl)-3-(pyridin-3-yl)propyl]-N³-[3-(1H-imidazol-4-yl)propyl]-guanidine The method of preparation is analogous to that of Example 14 (a), starting from 1.15 g (5 mmol) of 3-(4-fluorophenyl)-3-(pyridin-3-yl)-propylamine.

Yield: 1.15 g (47%) of a colourless, amorphous solid (foam).

C₂₈H₂₉FN₆O (484.6)

| ¹H-NMR data: | δ = 1.87 (m) 2 H, |
|---|---|
| (CDCl₃, TMS as internal standard) | 2.41 (dt) 2 H, |
| | 2.63 (t) 2 H, |
| | 3.1–3.8 (broad) 4 H, |
| | 4.06 (t) 1 H, |
| | 6.72 (s) 1 H, |
| | 6.95 (dd) 2 H, |
| | 7.1–7.6 (m) 8 H, |
| | 8.10 (d) 2 H, |
| | 8.41 (dd) 1 H, |
| | 8.45 (d) 1 H, |
| | 10.45 (broad) 1 H, replaceable by D₂O, ppm. |

(b) N¹-[3-(4-Fluorophenyl)-3-(pyridin-3-yl)propyl]-N²-[3-(1H-imidazol-4-yl)propyl]-guanidine The method of preparation is analogous to that of Example 14 (b), starting from 0.73 g (1.5 mmol) of N¹-benzoyl-N²-[3-(4-fluorophenyl)-3-(pyridin-3-yl)propyl]-N³-[3-(1H-imidazol-4-yl)-propyl]-guanidine.

Yield: 0.61 g (83%) of the trihydrochloride in the form of a hygroscopic, amorphous solid.

$C_{21}H_{25}FN_6 \times 3$ HCl (489.9).

MS (FAB method): m/z (rel. Int. [%]) = 381 ([M+H]⁺, 99), 214 (9), 186 (21), 109 (100), 100 (36).

| ¹H-NMR data: | δ = 1.84 (m) 2 H, |
|---|---|
| (DMSO-d₆, TMS as internal standard) | 2.38 (m) 2 H, |
| | 2.73 (t) 2 H, |
| | 3.09 (m) 2 H, |
| | 3.18 (dt) 2H, |
| | 4.56 (t) 1 H, |
| | 7.18 (dd) 2 H, |
| | 7.48 (s) 1 H, |
| | 7.51 (dd) 2 H, |
| | 7.60 (s) 2 H, replaceable by D₂O, |
| | 7.96 (dd) 1 H, |
| | 8.07 (m) 2 H, replaceable by D₂O, |
| | 8.54 (d) 1 H, |
| | 8.78 (d) 1 H, |
| | 9.00 (s) 1 H, |
| | 9.05 (s) 1 H, |
| | 14.45 (broad) 1 H, replaceable by D₂O. |
| | 14.8 (broad) 1 H, replaceable by D₂O, ppm. |

EXAMPLE 25

N¹-[3-(4-Fluorophenyl)-3-(pyridin-4-yl)propyl]-N²-[3-(1H-imidazol-4-yl)propyl]-guanidine

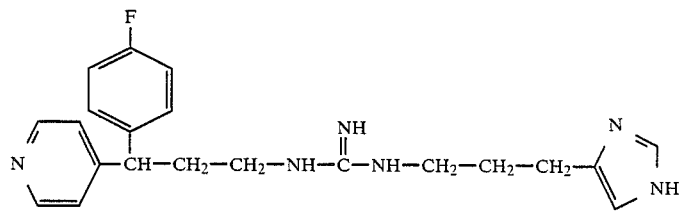

(a) N¹-Benzoyl-N²-[3-(4-fluorophenyl)-3-(pyridin-4-yl)propyl]-N³-[3-(1H-imidazol-4-yl)propyl]-guanidine The method of preparation is analogous to that of Example 14 a), starting from 1.15 g (5 mmol) of 3-(4-fluorophenyl)-3-(pyridin-4-yl)-propylamine.

Yield: 1.24 g (51%) of a colourless, amorphous solid (foam).

C₂₈H₂₉FN₆O (484.6).

| ¹H-NMR data: | δ = 1.87 (m) 2 H, |
|---|---|
| (CDCl₃, TMS as internal standard) | 2.39 (dt) 2 H, |
| | 2.63 (t) 2 H, |
| | 3.1–3.8 (broad) 4 H, |
| | 4.01 (t) 1 H, |
| | 6.72 (s) 1 H, |
| | 6.95 (dd) 2 H, |
| | 7.0—7.55 (m) 8 H, |
| | 8.09 (d) 2 H, |
| | 8.42 (d) 2H, |
| | 10.45 (broad) 1 H, replaceable |

(b) $N^1$-[3-(4-Fluorophenyl)-3-(pyridin-4-yl)propyl]-$N^2$-]3-(1H-imidazol-4-yl)propyl]-guanidine The method of preparation is analogous to that of Example 14 (b), starting from 0.73 g (1.5 mmol) of $N^1$-benzoyl-$N^2$-[3-(4-fluorophenyl)-3-(pyridin-4-yl)propyl]-$N^3$-[3-(1H-imidazol-4-yl)propyl]-guanidine.

Yield: 0.65 g (88%) of the trihydrochloride in the form of a hygroscopic, amorphous solid.
$C_{21}H_{25}FN_6 \times 3$ HCl (489.9).

MS (FAB method): m/z (rel. Int. [%])=381 ([M+H]$^+$, 73), 214 (22), 187 (34), 186 (8), 109 (100), 100 (36).

| $^1$H-NMR data: (DMSO-d$_6$, TMS as internal standard) | δ = 1.85 (m) 2 H, 2.39 (m) 2 H, 2.73 (t) 2 H, 3.11 (dt) 2 H, 3.19 (dt) 2 H, 4.64 (t) 1 H, 7.20 (dd) 2 H, 7.49 (s) 1 H, 7.51 (dd) 2 H, 7.63 (s) 2 H, replaceable by D$_2$O, 8.05–8.2 (m) 2 H, replaceable by D$_2$O, 8.07 (d) 2 H, 8.86 (d) 2 H, 9.06 (s) 1 H, 14.5 (broad) 2 H, replaceable by D$_2$O, ppm. |
|---|---|

EXAMPLE 26

$N^1$-[3-(1H-Imidazol-4-yl)propyl]-$N^2$-[3-(pyridin-2-yl)-3-(3-trifluoromethyl-phenyl)propyl]-guanidine

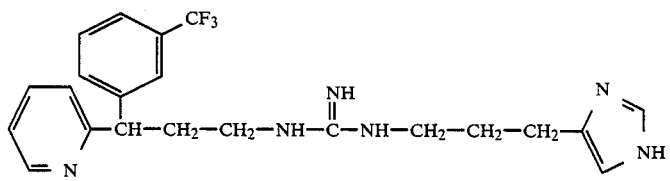

(a) $N^1$-Benzoyl-$N^2$-[3-(1H-imidazol-4-yl)propyl]-$N^3$-[3-(pyridin-2-yl)-3-(3-trifluoromethyl-phenyl)propyl]-guanidine The method of preparation is analogous to that of Example 14 (a) starting from 1.12 g (4 mmol) of 3-(pyridin-2-yl)-3-(3-trifluoromethyl-phenyl)-propylamine.

Yield: 1.2 g (56%) of a colourless, amorphous solid.
$C_{29}H_{29}F_3N_6O$ (534.6).

| $^1$H-NMR data: (CDCl$_3$, TMS as internal standard) | δ = 1.96 (m) 2 H, 2.32 (m) 1 H, 2.6–2.75 (m) 1 H, 2.70 (t) 2 H, 3.37 (broad) 2H, 3.55 (broad) 1 H, 3.90 (broad) 1 H, 4.26 (dd) 1 H, 6.74 (s) 1 H, 7.1–7.8 (m) 11 H, 8.12 (d) 2 H, 8.60 (d) 1 H, 10.3–10.9 (broad) 1 H, replaceable by D$_2$O, ppm |
|---|---|

(b) $N^1$-[3-(1H-imidazol-4-yl)propyl]-$N^2$-[3-(pyridin-2-yl)-3-(3-trifluoromethyl-phenyl)propyl]-guanidine The method of preparation is analogous to that of Example 14 (b), starting from 0.65 g (1.2 mmol) of $N^1$-benzoyl-$N^2$-[3-(1H-imidazol-4-yl)propyl]-$N^3$-[3-(pyridin-2-yl)-3-(3-trifluoromethyl-phenyl)propyl]-guanidine.

Yield: 0.6 g (93%) of the trihydrochloride in the form of hygroscopic, amorphous solid.
$C_{22}H_{25}F_3N_6 \times 3$ HCl (539.9) Molar mass (MS): Calc.: 430.20928, Found: 430.20926.

MS (FAB method): m/z (rel. Int. [%])=431 ([M+H]$^+$43), 264 (100), 237 (14), 236 (12), 109 (64), 100 (39).

| $^1$H-NMR data: (DMSO-d$_6$, TMS as internal standard) | δ = 1.85 (m) 2 H, 2.41 (m) 1 H, 2.64 (m) 1 H, 2.73 (t) 2 H, 3.0–3.3 (m) 4 H, 4.85 (t) 1 H, 7.4–8.2 (m) 11 H, 4 H replaceable by D$_2$O, 8.33 (dd) 1 H, 8.76 (d) 1 H, 9.07 (s) 1 H, 14.5 (broad) 1 H, replaceable by D$_2$O, 14.85 (broad) 1 H, replaceable by D$_2$O, ppm. |
|---|---|

EXAMPLE 27

$N^1$-[3-(1H-Imidazol-4-yl)propyl]-$N^2$-[3-(pyridin-2-yl)-3-(4-trifluoromethyl-phenyl)propyl]-guanidine

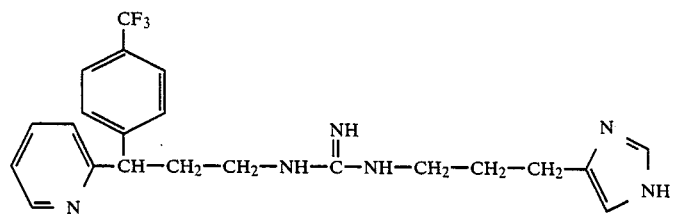

(a) N¹-Benzoyl-N²-[3-(1H-imidazol-4-yl)propyl]-N³-[3-(pyridin-2-yl)-3-(4-trifluoromethyl-phenyl)propyl]-guanidine The method of preparation is analogous to that of Example 14 (a), starting from 1.12 g (4 mmol) of 3-(pyridin-2-yl)-3-(4-trifluoromethyl-phenyl)-propylamine.

Yield: 1.0 g (47%) of a colourless, amorphous solid $C_{29}H_{29}F_3N_6O$ (534.6).

(b) N¹-[3-(1H-Imidazol-4-yl)propyl]-N²-[3-(pyridin-2-yl)-3-(4-trifluoromethyl-phenyl)propyl]-guanidine The method of preparation is analogous to that of Example 14 (b), starting from 0.65 g (1.2 mmol) of N¹-benzoyl-N²-[3-(1H-imidazol-4-yl)propyl]-N³-[3-(pyridin-2-yl)-3-(4-trifluoromethyl-phenyl)propyl]-guanidine.

Yield: 0.57 g (88%) of the trihydrochloride in the form of a hygroscopic, amorphous solid.
$C_{22}H_{25}F_3N_6 \times 3$ HCl (539.9).

| ¹H-NMR data: (DMSO-d₆, TMS as internal standard) | δ = 1.85 (m) 2 H, 2.1–3.45 (m) 8 H, 4.90 (t) 1 H, 7.4–8.2 (m) 11 H, 4 H replaceable by D₂O, 8.32 (dd) 1 H, 8.78 (d) 1 H, 9.05 (s) 1 H, 14.45 (broad) 1 H, replaceable by D₂O, 14.8 (broad) 1 H, replaceable by D₂O, ppm. |
|---|---|

EXAMPLE 28

N¹-[3-(4-Fluorophenyl)-3-phenyl-propyl]-N²-[3-(1H-imidazol-4-yl)propyl]-guanidine

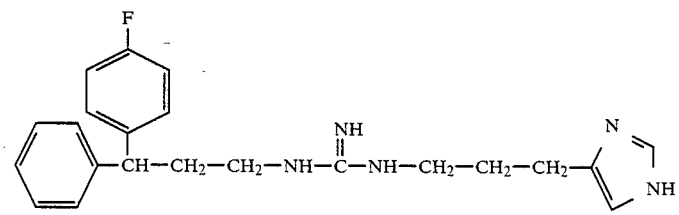

(a) N¹-Benzoyl-N²-[3-(4-fluorophenyl)-3-phenyl-propyl]-N³-[3-(1H-imidazol-4-yl)propyl]-guanidine.

The method of preparation is analogous to that of Example 14 (a), starting from 1.15 g (5 mmol) of 3-(4-fluorophenyl)-3-phenyl-propylamine.

Yield: 1.26 g (52%) of a colourless foam which crystallises with ethyl acetate/ether when triturated. Melting point 127° C.
$C_{29}H_{30}FN_5O$ (483.6).

| ¹H-NMR data: (CDCl₃, TMS as internal standard) | δ = 1.86 (m) 2 H, 2.40 (dt) 2 H, 2.63 (t) 2 H, 3.4 (broad) 2 H, 3.55 (broad) 2 H, 4.04 (t) 1 H, 6.71 (s) 1 H, 6.95 (dd) 2 H, 7.1–7.6 (m) 11 H, 8.12 (d) 2 H, 10.2–10.9 (broad) 1 H, replaceable by D₂O, ppm. |
|---|---|

(b) N¹-[3-(4-Fluorophenyl)-3-phenylpropyl]-N²-[3-(1H-imidazol-4-yl)propyl]-guanidine The method of preparation is analogous to that of Example 14 (b), starting from 0.58 g (1.2 mmol) of N¹-benzoyl-N²-[3-(4-fluorophenyl)-3-phenyl-propyl]-N³-[3-(1H-imidazol-4-yl)propyl]-guanidine.

Yield: 0.49 g (92%) of the dihydrochloride in the form of a hygroscopic, amorphous solid.
$C_{22}H_{26}FN_5 \times 2$ HCl (452.4).

MS (FAB method): m/z (rel. Int. [%])=380 ([M+H]⁺, 84), 272 (10), 185 (26), 109 (100), 100 (38), 95 (14), 91 (23).

| ¹H-NMR data: (DMSO-d₆, TMS as internal standard) | δ = 1.82 (m) 2 H, 2.2–2.35 (m) 2 H, 2.70 (t) 2 H, 3.02 (dt) 2 H, 3.16 (dt) 2 H, 4.16 (t) 1 H, 7.1–7.6 (m) 12 H, 2 H replaceable by D₂O, 7.92 (broad) 2 H, replaceable by D₂O, 9.03 (d) 1 H, 14.5 (broad) 2 H, replaceable by D₂O, ppm. |
|---|---|

EXAMPLE 29

N¹-[3,3-Bis-(4-fluorophenyl)-propyl]-N²-[3-(1H-imidazol-4-yl)propyl]-guanidine

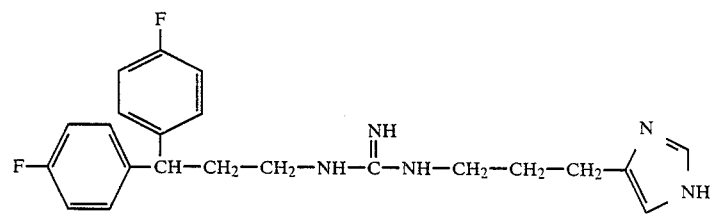

(a) N¹-Benzoyl-N²-[3,3-bis-(4-fluorophenyl)propyl]-N³-[3-(1H-imidazol-4-yl)propyl]-guanidine The method of preparation is analogous to that of Example 14 (a), starting from 1.24 g (5 mmol) of 3,3-bis-(4-fluorophenyl)-propylamine.

Yield: 1.35 g (54%) melting point 158° C. (ether).

$C_{29}H_{29}F_2N_5O$ (501.6) Analysis: Calc.: C 69.44 H 5.83 N 13.96. Found: C 69.83 H 5.88 N 14.09.

| $^1$H-NMR data: (CDCl$_3$, TMS as internal standard) | δ = 1.88 (m) 2 H, 2.3–2.45 (m) 2 H, 2.65 (t) 2 H, 3.35 (broad) 2 H, 3.55 (broad) 2 H, 4.04 (t) 1 H, 6.75 (s) 1 H, 6.96 (dd) 4 H, 7.1–7.5 (m) 8 H, 8.10 (m) 2 H, 10.5 (broad) 1 H, replaceable by D$_2$O, ppm. |
|---|---|

(b) $N^1$-[3,3-bis-(4-fluorophenyl)-propyl]-$N^2$-[3-(1H-imidazol-4-yl)propyl]-guanidine The method of preparation is analogous to that of Example 14 (b), starting from 0.6 g (1.2 mmol) of $N^1$-benzoyl-$N^2$-[3,3-bis-(4-fluorophenyl)-propyl]-$N^3$-[3-(1H-imidazol-4-yl)propyl]-guanidine.

Yield: 0.5 g (88%) of the dihydrochloride in the form of a hygroscopic, amorphous solid.
$C_{22}H_{25}F_2N_5 \times 2$ HCl (470.4).

| $^1$H-NMR data: (DMSO-d$_6$, TMS as internal standard) | δ = 1.83 (m) 2 H, 2.2–2.35 (m) 2 H, 2.71 (t) 2 H, 3.03 (dt) 2 H, 3.17 (dt) 2 H, 4.18 (t) 1 H, 7.1–7.55 (m) 11 H, 2 H replaceable by D$_2$O, 7.9 (broad) 2 H, replaceable by D$_2$O, 9.02 (d) 1 H, 14.5 (broad) 2 H, replaceable by D$_2$O, ppm. |
|---|---|

EXAMPLE 30
$N^1$-[3-(4-Chlorophenyl)-3-phenyl-propyl]-$N^2$-[3-(1H-imidazol-4-yl)propyl]-guanidine

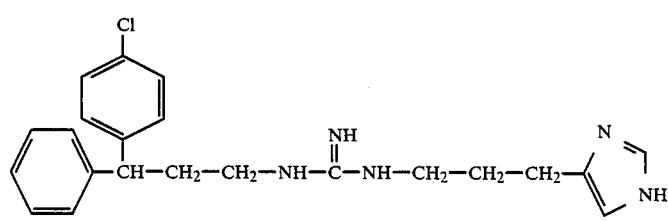

(a) $N^1$-Benzoyl-$N^2$-[3-(4-chlorophenyl)-3-phenyl-propyl]-$N^3$-[3-(1H-imidazol-4-yl)-propyl]-guanidine The method of preparation is analogous to that of Example 14 (a), starting from 1.23 g (5 mmol) of 3-(4-chlorophenyl)-3-phenyl-propylamine.

Yield: 0.95 g (38%) of a colourless, amorphous solid.

$C_{29}H_{30}ClN_5O$ (500.0).

| $^1$H-NMR data: (CDCl$_3$, TMS as internal standard) | δ = 1.86 (m) 2 H, 2.39 (dt) 2 H, 2.63 (m) 2 H, 3.1–3.8 (broad) 4 H, 4.02 (t) 1 H, 6.71 (s) 1 H, 7.05–7.55 (m) 13 H, 8.12 (d) 2 H, 10.4 (broad) 1 H, replaceable by D$_2$O, ppm. |
|---|---|

(b) $N^1$-[3-(4-Chlorophenyl)-3-phenyl-propyl]-$N^2$-[3-(1H-imidazol-4-yl)propyl]-guanidine The method of preparation is analogous to that of Example 14 (b) starting from 0.55 g (1.1 mmol) of $N^1$-benzoyl-$N^2$-[3-(4-chlorophenyl)-3-phenyl-propyl]-$N^3$-[3-(1H-imidazol-4-yl)propyl]-guanidine.

Yield: 0.45 g (91%) of the dihydrochloride in the form of a hygroscopic, amorphous solid.
$C_{22}H_{26}ClN_5O \times 2$ HCl (449.4).

MS (FAB method): m/z (rel. Int. [%])=396 ([M+H]$^+$, 38), 201 (10), 109 (100), 100 (41), 91 (25).

| $^1$H-NMR data: (DMSO-d$_6$, TMS as internal standard) | δ = 1.83 (m) 2 H, 2.26 (dt) 2 H, 2.71 (t) 2 H, 3.03 (dt) 2 H, 3.17 (dt) 2 H, 4.18 (t) 1 H, 7.2–7.6 (m) 12 H, 2 H replaceable by D$_2$O, 7.96 (broad) 2 H, replaceable by D$_2$O, 9.04 (d) 1 H, 14.5 (broad) 2 H, replaceable by D$_2$O, ppm. |
|---|---|

EXAMPLE 31
$N^1$-[3-(3,4-Dichlorophenyl)-3-phenyl-propyl]-$N^2$-[3-(1H-imidazol-4-yl)propyl]-guanidine

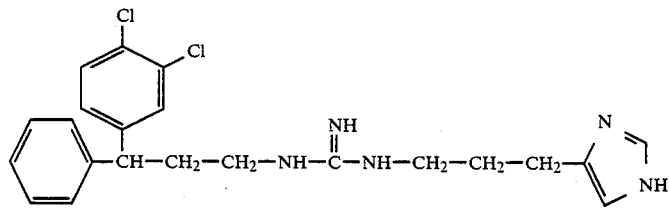

(a) $N^1$-Benzoyl-$N^2$-[3-(3,4-dichlorophenyl)-3-phenyl-propyl]-$N^3$-[3-(1H-imidazol-4-yl)propyl]-guanidine The method of preparation is analogous to that of Example 14 (a), starting from 1.4 g (5 mmol) of 3-(3,4-dichlorophenyl)-3-phenyl-propylamine.

Yield: 1.2 g (45%) of a colourless amorphous solid.

C$_{29}$H$_{29}$Cl$_2$N$_5$O (534.5).

| $^1$H-NMR data: (CDCl$_3$, TMS as internal standard) | δ = | 1.88 (m) 2 H, 2.40 (dt) 2 H, 2.66 (m) 2 H, 3.1–3.8 (broad) 4 H, 4.03 (t) 1 H, 6.76 (s) 1 H, 7.09 (d) 1 H, 7.15–7.5 (m) 11 H, 8.12 (d) 2 H, 10.5 (broad) 1 H, replaceable by D$_2$O, ppm. |
|---|---|---|

(b) N$^1$-[3-(3,4-Dichlorophenyl)-3-phenyl-propyl]-N$^2$-[3-(1H-imidazol-4-yl)propyl]-guanidine The method of preparation is analogous to that of Example 14 (b) starting from 0.75 g (1.4 mmol) of N$^1$-benzoyl-N$^2$-[3-(3,4-dichlorophenyl)-3-phenyl-propyl]-N$^3$-[3-(1H-imidazol-4-yl)propyl]-guanidine.

Yield: 0.57 g (87%) of the dihydrochloride in the form of a hygroscopic, amorphous solid.

C$_{22}$H$_{25}$Cl$_2$N$_5$×2 HCl (467.9).

MS (FAB method): m/z (rel. Int. [%])=430 ([M+H]$^+$, 19), 165 (16), 109 (100), 100 (34), 91 (21).

| $^1$H-NMR data: (DMSO-d$_6$, TMS as internal standard) | δ = | 1.84 (m) 2 H, 2.28 (dt) 2 H, 2.72 (t) 2 H, 3.04 (dt) 2 H, 3.17 (dt) 2 H, 4.25 (t) 1 H, 7.15–7.7 (m) 11 H, 2H replaceable by D$_2$O, 8.02 (m) 2 H, replaceable by D$_2$O, 9.06 (s) 1 H, 14.6 (broad) 2 H, replaceable by D$_2$O, ppm. |
|---|---|---|

EXAMPLE 32

N$^1$-[3-Hydroxy-3-(4-fluorophenyl)-3-(pyridin-2-yl)propyl]-N$^2$-[3-(1H-imidazol-4-yl)propyl]-guanidine

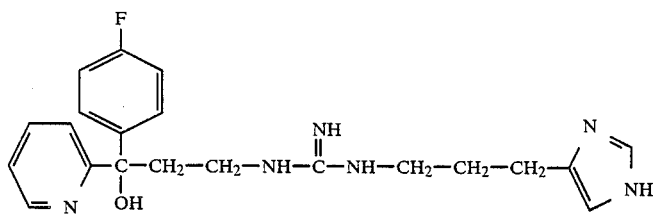

(a) N$^1$-Benzoyl-N$^2$-[3-hydroxy-3-(4-fluorophenyl)-3-(pyridin-2-yl)propyl]-N$^3$-[3-(1H-imidazol-4-yl)propyl]-thiourea 3.69 g (15 mmol) of 3-hydroxy-3-(4-fluorophenyl)-3-(pyridin-2-yl)-propylamine and 2.45 g (15 mmol) of benzoyl isothiocyanate are heated under reflux in 150 ml of chloroform for 40 minutes. The solvent is then distilled off under vacuum and the residue is brought to crystallisation with ether.

Yield: 5.4 g (88%) of a colourless solid which melts at 138°–139° C. after recrystallisation from ethanol/water.

C$_{22}$H$_{20}$FN$_3$O$_2$S (409.5) Analysis: Calc.: C 64.53 H 4.92 N 10.26. Found: C 64.70 H 4.91 N 10.18.

(b) N-[3-Hydroxy-3-(4-fluorophenyl)-3-(pyridin-2-yl)propyl]-thiourea 3.07 g (7.5 mmol) of N$^1$-benzoyl-N$^2$-[3-hydroxy-3-(4-fluorophenyl)-3-(pyridin-2-yl)propyl]-N$^3$-[3-(1H-imidazol-4-yl)propyl]-guanidine and 2.1 g of potassium carbonate are together heated under reflux in a mixture of 30 ml of water and 70 ml of methanol for one hour. 1.92 g (84%) of a colourless solid precipitates after concentration by evaporation under vacuum, and melts at 148° to 149° C. after recrystallisation from ethanol/water.

C$_{15}$H$_{16}$FN$_3$OS (305.4) Analysis: Calc.: C 59.00 H 5.28 N 13.76. Found: C 59.20 H 5.33 N 13.71.

(c) N-[3-Hydroxy-3-(4-fluorophenyl)-3-(pyridin-2-yl)propyl]-S-methyl-isothiuronium iodide 1.53 g (5 mmol) of N-[3-hydroxy-3-(4-fluorophenyl)-3-(pyridin-2-yl)propyl]-thiourea are stirred up with 0.4 ml of methyl iodide for 12 hours at room temperature. After concentration by evaporation, the isothiuronium iodide crystallises when triturated with ether and a small quantity of ethanol.

Yield: 1.79 g (84%). Melting point after crystallisation from acetone/ether and drying of the crystals at 60° C./$_{0.05}$: 114°–115° C.

C$_{16}$H$_{18}$FN$_3$OS×HI (447.3) Analysis: Calc.: C 42.96 H 4.28 N 9.39. Found: C 42.58 H 4.25 N 9.23.

| $^1$H-NMR data: (DMSO-d$_6$, TMS as internal standard) | δ = | 2.55 (s) 3 H, 2.62 (m) 1 H, 2.77 (m) 1 H, 3.23 (m) 2 H, 6.21 (s) 1 H, replaceable by D$_2$O, 7.14 (dd) 2 H, 7.29 (dd) 1 H, 7.51 (dd) 2 H, 7.64 (d) 1 H, 7.82 (dd) 1 H, 8.54 (d) 1 H, 9.0 (broad) 2 H, replaceable by D$_2$O, 9.25 (broad) 1 H, replaceable by D$_2$O, ppm. |
|---|---|---|

(d) N$^1$-[3-Hydroxy-3-(4-fluorophenyl)-3-(pyridin-2-yl)propyl]-N$^2$-[3-(1H-imidazol-4-yl)propyl]-guanidine 1.5 g (3.5 mmol) of N-[3-hydroxy-3-(4-fluorophenyl)-3-(pyridin-2-yl)propyl]-S-methyl-isothiuronium iodide and 0.48 g (3.8 mmol) of 3-(1H-imidazol-4-yl)-propylamine are stirred up in 50 ml of pyridine at 80° C. for 5 hours. After concentration of the reaction mixture by evaporation under vacuum, the product is isolated and purified by preparative layer chromatography on gypsum-containing silica gel 60 PF$_{254}$ (solvent: chloroform/methanol, 90/10, ammoniacal atmosphere).

Yield: 1.0 g (55%) of the hydriodide in the form of an amorphous solid.

C$_{21}$H$_{25}$FN$_6$O×HI (524.4).

MS (FAB method): m/z (rel. Int. [%])=397 ([M+H]$^+$, 89), 230 (66), 212 (22), 200 (42), 185 (13), 152 (11), 151 (15), 109 (100), 100 (44), 95 (12).

| | |
|---|---|
| ¹H-NMR data: (DMSO-d₆, TMS as internal standard | δ = 1.75 (m) 2 H, 2.5–2.9 (m) 4 H, 3.07 (m) 2 H, 3.14 (dt) 2 H, 6.22 (s) 1 H, replaceable by D₂O, 6.91 (s) 1 H, 7.11 (dd) 2 H, 7.27 (dd) 1 H, 7.4 (m) 4 H, replaceable by D₂O, 7.52 (dd) 2 H, 7.64 (d) 1 H, 7.78 (dd) 1 H, 7.81 (s) 1 H, 8.53 (d) 1 H, ppm. |

EXAMPLE 33

N¹-[3-(4-Methoxyphenyl)-3-(pyridin-2-yl)propyl]-N²-[3-(1H-imidazol-4-yl)propyl]-guanidine

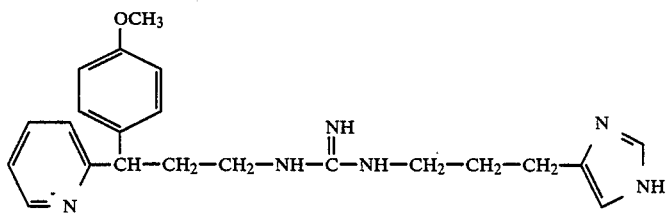

(a) N-[3-(4-Methoxyphenyl)-3-(pyridin-2-yl)propyl]-S-methyl-isothiuronium iodide The method of preparation is analogous to that of Example 32 a–c, starting from 3.63 g (15 mmol) of 3-(4-methoxyphenyl)-3-(pyridin-2-yl)-propylamine. The isothiuronium iodide crystallises when the foam initially obtained is triturated with ether.

Yield: 3.2 g (72%) of colourless crystals, melting point 123°–125° C. (acetone/ether).

C₁₇H₂₁N₃OS×HI (443.4) Analysis: Calc.: C 46.06 H 5.00 N 9.48. Found: C 45.93 H 5.00 N 9.44.

| | |
|---|---|
| ¹H-NMR data: | δ = 2.2–2.75 (m) 2 H, |
| (DMSO-d₆, TMS as internal standard | 2.59 (s) 3 H, 3.0–3.4 (m) 2 H, 3.72 (s) 3 H, 4.01 (t) 1 H, 6.86 (d) 2 H, 7.05–7.45 (m) 2 H, 7.25 (d) 2 H, 7.72 (dd) 1 H, 8.61 (d) 1 H, 9.2 (broad) 3 H, replaceable by D₂O, ppm. |

(b) N¹-[3-(4-Methoxyphenyl)-3-(pyridin-2-yl)propyl]-N²-[3-(1H-imidazol-4-yl)propyl]-guanidine 2.66 g (6 mmol) of N-[3-(4-methoxyphenyl)-3-(pyridin-2-yl)-propyl]-S-methyl-isothiuronium iodide and 0.8 g (6.4 mmol) of 3-(1H-imidazol-4-yl)-propylamine are heated together under reflux in 50 ml of acetonitrile. After concentration of the reaction mixture by evaporation under vacuum, the product is isolated by preparative layer chromatography as in Example 32 (d).

Yield: 1.96 g (63%) of the hydriodide in the form of an amorphous solid.

C₂₂H₂₈N₆O×HI (520.4).

MS (FAB method): m/z (rel. Int. [%])=393 ([M+H]⁺71), 226 (100), 199 (10), 198 (9), 184 (11), 167 (12), 118 (12), 109 (58), 100 (36).

| | |
|---|---|
| ¹H-NMR data: (DMSO-d₆, TMS as internal standard | δ = 1.75 (m) 2 H, 2.19 (m) 1 H, 2.45 (m) 1 H, 2.51 (t) 2 H, 3.03 (dt) 2 H, 3.17 (dt) 2 H, 3.70 (s) 3 H, 4.11 (t) 1 H, 6.80 (m) 1 H, 6.84 (d) 2 H, 7.18–7.27 (m) 4 H, 7.4 (broad) 4 H, replaceable by D₂O, 7.52 (d) 1 H, 7.69 (dd) 1 H, 8.51 (d) 1 H, 11.85 (broad) 1 H, replaceable by D₂O, ppm. |

EXAMPLE 34

N¹-[3-(4-Hydroxyphenyl)-3-(pyridin-2-yl)propyl]-N²-[3-(1H-imidazol-4-yl)propyl]-guanidine

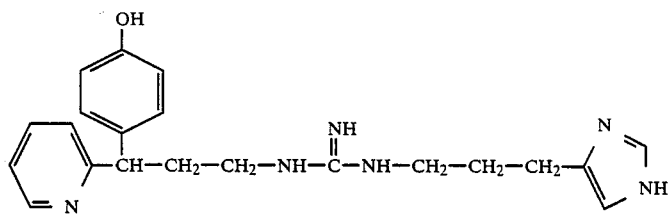

(a) N¹-Benzoyl-N²-[3-(1H-imidazol-4-yl)propyl]-N³-[3-(4-methoxyphenyl)-3-(pyridin-2-yl)propyl]-guanidine The method of preparation is analogous to that of Example 14 (a), starting from 1.21 g (5 mmol) of 3-(4-methoxyphenyl)-3-(pyridin-2-yl)-propylamine.

Yield: 1.19 g (48%) of a colourless amorphous solid (foam).

C₂₉H₃₂N₆O₂ (496.6).

| | |
|---|---|
| ¹H-NMR data: (CDCl₃, TMS as internal standard) | δ = 1.95 (m) 2 H, 2.29 (broad) 1 H, 2.5–2.75 (m) 3 H, 3.1–4.1 (broad) 4 H, 3.76 (s) 3 H, |

4.15 (dd) 1 H,
6.72 (s) 1 H,
6.82 (d) 2 H,
7.0–7.75 (m) 9 H,
8.12 (d) 2 H,
8.55 (d) 1 H,
10.75 (broad) 1 H, replaceable by D$_2$O, ppm.

(b) $N^1$-[3-(4-hydroxyphenyl)-3-(pyridin-2-yl)propyl]-$N^2$-[3-(1H-imidazol-4-yl)propyl]-guanidine 0.6 g (1.2 mmol) of $N^1$-benzoyl-$N^2$-[3-(1H-imidazol-4-yl)propyl]-$N^3$-[3-(4-methoxyphenyl)-3-(pyridin-2-yl)propyl]-guanidine are heated under reflux in 48% aqueous hydrobromic acid for 10 hours. The acid solution is diluted with water, extracted four times with ether and evaporated to dryness under vacuum. After drying in a high vacuum, 0.63 g (85%) of the trihydrobromide is obtained as residue in the form of a hygroscopic, amorphous solid.

Alternatively, $N^1$-[3-(4-hydroxyphenyl)-3-(pyridin-2-yl)propyl]-$N^2$-[3-(1H-imidazol-4-yl)propyl]-guanidine may be prepared by the following process:

0.9 g (1.7 mmol) of $N^1$-[3-(4-methoxyphenyl)-3-(pyridin-2-yl)propyl]-$N^2$-[3(1H-imidazol-4-yl)propyl]-guanidine hydriodide (Example 33) is converted into the picrate by reaction with ethanolic picric acid solution and is then converted into the trihydrochloride by extraction of the picric acid from a hydrochloric acid solution with ether and concentration of the aqueous solution by evaporation under vacuum. The amorphous solid obtained is heated under reflux in 48% aqueous hydrobromic acid for 10 hours. After concentration of the reaction mixture by evaporation under vacuum and drying of the residue in a high vacuum, 0.84 g (80%) of the trihydrobromide is obtained as residue in the form of a hygroscopic, amorphous solid.

$C_{21}H_{26}N_6O \times 3$ HBr (621.2).

MS (FAB method): m/z (rel. Int. [%])=379 ([M+H]$^+$, 86), 213 (14), 212 (87), 195 (15), 189 (11), 168 (14), 167 (16), 157 (17), 151 (14), 131 (12), 126 (13), 118 (15), 117 (11), 115 (45), 110 (22), 109 (100), 107 (15), 100 (44), 95 (29).

| $^1$H-NMR data: DMSO-d$_6$, TMS as internal standard | $\delta$ = 1.82 (m) 2 H, 2.25–2.65 (m) 2 H, 2.70 (t) 2 H, 3.10 (dt) 2 H, 3.19 (dt) 2 H, 4.43 (t) 1 H, 6.75 (d) 2 H, 7.24 (d) 2 H, 7.43 (m) 2 H, replaceable by D$_2$O, 7.51 (s) 1 H, 7.58 (m) 2 H, replaceable by D$_2$O, 7.79 (dd) 1 H, 7.99 (d) 1 H, 8.40 (dd) 1 H, 8.78 (d) 1 H, 9.09 (s) 1 H, 9.5 (broad) 1 H, replaceable by D$_2$O, 14.06 (broad) 1 H, replaceable by D$_2$O, 14.24 (broad) 1 H, replaceable by D$_2$O, ppm. |
|---|---|

We claim:

1. An imidazolylguanidine derivative corresponding to the formula I

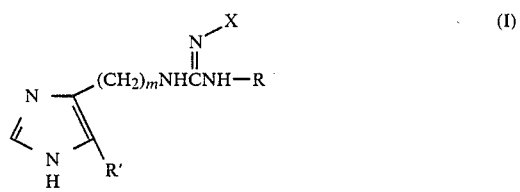

wherein R denotes the group

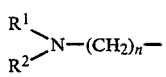

in which $R^1$ represents an unsubstituted or a mono- to tri-substituted phenyl group or an unsubstituted or a mono- to tri-substituted pyridine ring, wherein the substituents on $R^1$ are selected from halogen, $C_1$–$C_3$ alkyl and $C_1$–$C_3$ alkoxy, $R^2$ represents a hydrogen atom, a $C_1$–$C_3$ alkyl group, a phenyl group, a mono- to tri-substituted phenyl group, wherein the substituents are as defined above, an unsubstituted or a mono- to tri-substituted benzyl group, wherein the substituents on the benzyl group are selected from halogen and $C_1$–$C_3$ alkoxy, or an unsubstituted or a mono- to tri-substituted heteroarylmethyl group selected from thiophenylmethyl, furanmethyl and pyridine methyl, wherein the substituents on the heteroarylmethyl group are selected form halogen, $C_1$–$C_3$ alkyl and $C_1$–$C_3$ alkoxy, and n has the value 2, 3 or 4, or wherein R denotes the group

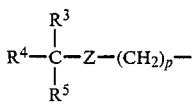

wherein $R^3$ represents an unsubstituted or a mono- to tri-substituted phenyl group or an unsubstituted or a mono- to tri-substituted pyridine ring, wherein the substituents on $R^3$ are selected from halogen, $C_1$–$C_3$ alkyl and $C_1$–$C_3$ alkoxy, and wherein when $R^3$ is phenyl, the substituents thereon are further selected from trifluoromethyl and hydroxyl, $R^4$ represents a hydrogen atom or an optionally mono- to tri-substituted phenyl group, wherein the substituents on $R^4$ are the same as in $R^3$ when $R^3$ is phenyl, $R^5$ represents a hydrogen atom or a methyl or hydroxyl group and Z represents a single bond or a oxygen atom, and p has the value 2 or 3, X denotes a hydrogen atom or a benzoyl group, m has the value 2 or 3 and R' denotes a hydrogen atom or a methyl group, or a physiologically acceptable salt thereof.

2. An imidazolylguanidine derivative according to claim 1, wherein R denotes the group

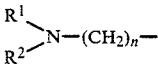

wherein $R^1$ stands for an unsubstituted or a mono- to tri-substituted pyridine ring, $R^2$ stands for an optionally mono- to tri-substituted heteroarylmethyl group, n has the value 2, 3 or 4, X and R' stand each for a hydrogen atom and m has the value 3.

3. An imidazolylguanidine derivative according to claim 1, wherein R denotes the group

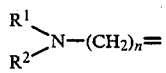

wherein $R^1$ stands for an unsubstituted or a mono- to tri-substituted phenyl ring, $R^2$ stands for an unsubstituted or a mono- to tri-substituted heteroaryl group, n has the value 2, 3 or 4, X and R' stand each for a hydrogen atom and m has the value 3.

4. An imidazolylguanidine derivative according to claim 1, wherein R denotes the group

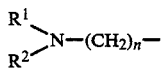

wherein $R^1$ stands for an unsubstituted or a mono- to tri-substituted pyridine ring and $R^2$ stands for a hydrogen atom, n has the value 2, 3 or 4, X and R' stand each for a hydrogen atom and m has the value 3.

5. An imidazolylguanidine derivative according to claim 1, wherein R denotes the group

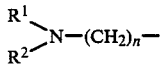

wherein $R^1$ stands for an unsubstituted or a mono- to tri-substituted pyridine ring and $R^2$ stands for an unsubstituted or a mono- to tri-substituted phenyl group, n has the value 2, 3 or 4, X and R' stand each for a hydrogen atom and m has the value 3.

6. An imidazolylguanidine derivative according to claim 1, wherein R

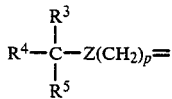

wherein $R^3$ and $R^4$, which may be identical or different, stand each for an unsubstituted or a mono- to tri-substituted phenyl group, $R^5$ stands for a hydrogen atom or a methyl group and Z stands for a single bond, p has the value 2 or 3, X and R's stand each for a hydrogen atom and m has the value 3.

7. An imidazolylguanidine derivative according to claim 1, wherein R denotes the group

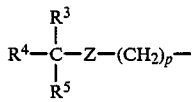

wherein $R^4$ stands for an unsubstituted or a mono- to tri-substituted phenyl group and $R^3$ stands for an unsubstituted or a mono- to tri-substituted pyridine ring, $R^5$ stands for a hydrogen atom or a methyl or hydroxyl group, Z stands for a single bond, p has the value 2 or 3, X stands for a hydrogen atom and R' stands each for a hydrogen atom and m has the value 3.

8. An imidazolylguanidine derivative according to claim 1, wherein R denotes the group

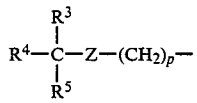

wherein $R^3$ stands for an unsubstituted or a mono-to tri-substituted pyridine ring, $R^4$ and $R^5$ stand each for a hydrogen atom, Z stands for a single bond and p has the value 2, 3 or 4, X and R' stand each for a hydrogen atom and m has the value 3.

9. An imidazolylguanidine derivative according to claim 1, wherein R denotes the group

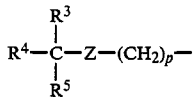

wherein $R^3$ and $R^4$, which maybe identical or different, stand each for an unsubstituted or a mono- to tri-substituted phenyl ring, $R^5$ stands for a hydrogen atom and Z stands for an oxygen atom, p has the value 2 or 3, X and R' stand each for a hydrogen atom and m has the value 3.

10. $N^1$-[3-(1H-Imidazol-4-yl)propyl]-$N^2$-[3-(3,4-dichlorophenyl)-3-(pyridin-2-yl)propyl]-guanidine or a physiologically acceptable salt thereof.

11. $N^1$-[3-(1H-Imidazol-4-yl)propyl]-$N^2$-[3-(3,4-difluorophenyl)-3-(pyridin-2-yl)propyl]-guanidine or a physiologically acceptable salt thereof.

12. $N^1$-[3-(1H-Imidazol-4-yl)propyl]-$N^2$-[3-(4-fluorophenyl)-3-phenylpropyl]-guanidine or a physiologically acceptable salt thereof.

13. $N^1$-[3-(1H-Imidazol-4-yl)propyl]-$N^2$-[3-(2,4-dichlorophenyl)-3-(pyridin-2-yl)-propyl]-guanidine or a physiologically acceptable salt thereof.

14. $N^1$-[3-(1H-Imidazol-4-yl)propyl]-$N^2$-[3-(3-chlorophenyl)-3-(pyridin-2-yl)propyl]-guanidine or a physiologically acceptable salt thereof.

15. $N^1$-[3-(1H-Imidazol-4-yl)propyl]-$N^2$-[3-(4-fluorophenyl)-3-(pyridin-3-yl)propyl]-guanidine or a physiologically acceptable salt thereof.

16. $N^1$-[3-(1H-Imidazol-4-yl)propyl]-$N^2$-[3-(3,5-difluorophenyl)-3-(pyridin-2-yl)propyl]-guanidine or a physiologically acceptable salt thereof.

17. Imidazolylguanidine derivatives corresponding to the formula I

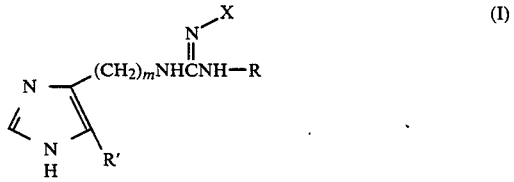

wherein R denotes the group

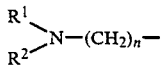

in which $R^1$ stands for a phenyl or a pyridine group, which may be unsubstituted or mono-substituted with a halogen atom, $R^2$ stands for a hydrogen atom or a phenyl ring, a benzyl group or a thiophenylmethyl group, which may be unsubstituted or mono-substituted with a halogen atom, and n has the value 2, 3 or 4, or wherein R denotes the group

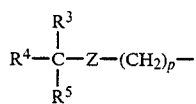

wherein $R^3$ stands for a phenyl or pyridine ring, which may be unsubstituted or substituted by one or two substituents selected from halogen atoms and methyl groups, $R^4$ stands for a hydrogen atom, a phenyl group, or a phenyl group optionally substituted by one or two halogen atoms, a methoxy group, a methyl group or a trifluoromethyl group, $R^5$ stands for a hydrogen atom or a methyl or hydroxy group and Z stands for a single bond or an oxygen atom, and p has the value 2 or 3, X denotes a hydrogen atom or a benzoyl group, m has the value 2 or 3 and R' denotes a hydrogen atom or a methyl group, or a physiologically acceptable salt thereof.

18. A pharmaceutical composition useful in the treatment of cardiac disease, hypertension and arterial occlusion, comprising a pharmaceutically effective amount of a compound according to claims 2, 3, 4, 5, 6, 7, 8, 9, 10, 11, 12, 13, 14, 15, 16 or 1 and at least one inert, pharmaceutically acceptable carrier or an inert, pharmaceutically acceptable diluent.

* * * * *